US011217328B2

(12) United States Patent
Hangartner et al.

(10) Patent No.: US 11,217,328 B2
(45) Date of Patent: Jan. 4, 2022

(54) EPITOPE MAPPING METHOD

(71) Applicant: The Scripps Research Institute, La Jolla, CA (US)

(72) Inventors: Lars Hangartner, San Diego, CA (US); Andrew Ward, San Diego, CA (US); Matteo Bianchi, San Diego, CA (US); Hannah Turner, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 9 days.

(21) Appl. No.: 16/388,681

(22) Filed: Apr. 18, 2019

(65) Prior Publication Data

US 2019/0325985 A1 Oct. 24, 2019

Related U.S. Application Data

(60) Provisional application No. 62/660,024, filed on Apr. 19, 2018.

(51) Int. Cl.
| | |
|---|---|
| *G16B 15/00* | (2019.01) |
| *G16B 25/20* | (2019.01) |
| *G01N 33/564* | (2006.01) |
| *H01J 37/26* | (2006.01) |
| *H01J 49/00* | (2006.01) |

(52) U.S. Cl.
CPC ............ *G16B 15/00* (2019.02); *G01N 33/564* (2013.01); *G16B 25/20* (2019.02); *H01J 37/26* (2013.01); *H01J 49/0027* (2013.01)

(58) Field of Classification Search
None
See application file for complete search history.

(56) References Cited

PUBLICATIONS

Bianchi et al., "Electron-Microscopy-Based Epitope Mapping Defines Specificities of Polyclonal Antibodies Elicited during HIV-1 BG505 Envelope Trimer Immunization," Immunity, Aug. 21, 2018; 49:288-300.

*Primary Examiner* — Nicole Kinsey White
(74) *Attorney, Agent, or Firm* — Umberg Zipser LLP

(57) ABSTRACT

Provided herein are methods for mapping antibody binding to an immunogen, comprising: immunizing a subject with an immunogen and obtaining sera from the immunized subject at multiple time intervals following immunization, wherein the sera comprises antibodies that are used to form one or more immune complexes with the immunogen; isolating the one or more immune complexes formed by the serum derived antibodies bound to the immunogen; imaging, by electron microscopy, the one or more immune complexes in each of the time intervals, to obtain structural images formed between the immunogen and serum antibodies; determining, from the plurality of structural images, immunogen-antibody binding site for each of the immune complexes obtained at the plurality of time intervals; mapping immunogen-antibody binding by measuring differences in structural images obtained at different time intervals to determine immunogen-antibody binding over multiple time intervals.

12 Claims, 8 Drawing Sheets

Novel approach

Proposed New Analysis

EPITOPE MAPPING METHOD

This application claims priority to our U.S. provisional application with the Ser. No. 62/660,024, filed Apr. 19, 2018.

STATEMENT REGARDING FEDERALLY SPONSORED RESEARCH OR DEVELOPMENT

This invention was made with government support under UM1AI100663 awarded by the National Institutes of Health. The United States government has certain rights in the invention.

FIELD OF THE INVENTION

The present disclosure relates to the characterization of epitopes and to vaccine design.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

One of the rate-limiting steps in the iterative vaccine development approach is in analysis of the polyclonal immune response elicited by immunization. Serum neutralization assays and enzyme-linked immunosorbent assays (ELISA) are typically used as readouts of the epitopes recognized by elicited antibodies. Recently methods such as use of deep sequencing of the B cell receptor (BCR) repertoire of responding B cells have been introduced; however, this method has considerable limitations because the heavy-light chain pairing is usually lost. Similarly, next generation sequencing (NGS) analyses can be used to study responses but it requires a considerable amount of pre-existing knowledge to interpret the sequencing data. Thus, to gain a detailed picture of an immunogen complex, monoclonal antibodies are generated from the polyclonal antibodies, and then the structure of the monoclonal antibody in complex with the immunogen is determined. This process is time consuming and limited to a relatively small number of samples. Such analyses typically focus on antibodies with a biological function (e.g. neutralization) and often leave the remainder of the humoral immune response less well investigated. Due to the high cost and labor involved, unsuccessful outcomes of vaccination experiments are hardly ever analyzed in detail, and the reasons for failure of a given immunogen to generate neutralizing response continues to remain unknown.

Thus, there remains a need in the art for new techniques and methods for identifying the specificities of antibodies in a time and cost-effective manner.

SUMMARY OF THE DISCLOSURE

Various embodiments disclosed herein include a method of mapping immune response to an immunogen, comprising: immunizing a subject with an immunogen and obtaining sera from the immunized subject at multiple time intervals following immunization, wherein the sera comprises one or more immune complexes between the immunogen and serum antibodies, imaging, by electron microscopy, the sera obtained from the immunized subject in each of the time intervals, to obtain structural images of the one or more immune complexes formed between the immunogen and serum antibodies; mapping immune response to the immunogen by measuring differences in structural images obtained at different time intervals to simultaneously visualize diverse antibodies targeting distinct epitopes in the immunized subjects. In one embodiment, the antibody may be an immunoglobulin, such as IgA (immunoglobin A), IgD (immunoglobin D), IgE (immunoglobin E), IgG (immunoglobin G), IgM (immunoglobin M), or combinations thereof. In one embodiment, the immunoglobulin is purified from the plasma, sera, tissue, secretions, or feces of the subject. In one embodiment, the binding step is performed by incubating the Fab and the immunogen together in a solution. In one embodiment, the immune complex is purified by a chromatographic method. In one embodiment, the chromatographic method if size exclusion chromatography (SEC). In one embodiment, the immune complex is analyzed by an imaging method or a spectrometric method. In one embodiment, the imaging method is electron microscopy (EM) or cryoEM. In one embodiment, the immune complex is analyzed by Mass Spectrometry, next generation sequencing (NGS), MS/MS and/or NGS-assisted MS/MS. In one embodiment, the subject is a vertebrate. In one embodiment, the subject is a mammal. In one embodiment, the subject is a human. In another embodiment, the subject is a rabbit, mouse, humanized mouse, rat, humanized rat, cow, and/or monkey. In one embodiment, the rapid analysis of the immune complex allows for characterization and quantification of antibody responses elicited by immunization or infection. In one embodiment, the method provides real time analysis of ongoing immunization experiments. In one embodiment, the method provides analysis of the immune response following infection with pathogens. In one embodiment, the ongoing immunization experiments comprises human vaccine trials. In one embodiment, the method provides cues for the improvement of the immunogen in case of failure of the human vaccine trial. In one embodiment, the immunogen is a recombinant immunogen. In one embodiment, the immunogen is an epitope and/or an antigen. In one embodiment, the method maps the epitopes recognized by the antibody.

Embodiments of the present disclosure also include a method comprising: generating an immune complex; imaging the immune complex; processing the images to generate 2D and 3D class averages and quantification thereof; and qualitative and/or quantitative assaying of the immune complex. In one embodiment, the qualitative and/or quantitative assaying of the immune complex is by electron microscopy (ES), mass spectrometry, tandem mass spectrometry, next generation sequencing, or combinations thereof. In one embodiment, the immune complex is a polyclonal immune complex. In one embodiment, the immune complex comprises an antigen-antibody complex. In one embodiment, the method characterizes the epitopes recognized by the antibody in the antigen-antibody complex. In one embodiment, the method further comprises purifying the immune complex prior to the imaging step.

Embodiments of the present disclosure further include a method for characterizing epitopes recognized by polyclonal antibodies, comprising: preparation and purification of the polyclonal immune complexes; imaging of the complexes; processing of the images including generation of 2D and 3D class averages and quantification thereof; and qualitative and/or quantitative assaying of the antibodies in the immune complexes by mass spectrometry and/or next generation sequencing (NGS).

Various embodiments of the present disclosure also include a method of forming an immune complex comprising: providing an immunoglobulin (Ig) antibody; enzymatically digesting the Ig into fragment antigen binding (Fab) and complexing the Fab with a soluble pathogen and/or antigen; quantifying the specific Ig content for immune complex formation; and forming the immune complex by incubating the pathogen and/or antigen with an excess of Fab. In one embodiment, the enzyme used for digestion is in solution. In one embodiment, the enzyme used for digestion is immobilized on a resin. In one embodiment, the enzymatic digestion is done by a protease. In one embodiment, the Ig is IgA (immunoglobin A), IgD (immunoglobin D), IgE (immunoglobin E), IgG (immunoglobin G), IgM (immunoglobin M), or combinations thereof. In one embodiment, the IgA is enzymatically digested using IgA proteases selected from the group comprising of but not limited to *Clostridium ramosum, Neisseria gonorrhoeae, Neisseria meningitidis, Haemophilus influenzae,* and *Streptococcus pneumonia,* or combinations thereof. In one embodiment, the IgM is enzymatically digested using Pepsin, Trypsin, species-specific bacterial IgM proteases or other proteases. In one embodiment, the IgG is enzymatically digested using papain, ficin, IdeS, IdeZ or other suitable protease either as a free enzyme or as enzyme bound to a substrate. In one embodiment, the antigen is an immunogen. In one embodiment, the pathogen and/or antigen is a HIV envelope protein. In one embodiment, the antigen is expressed as a BG505 SOSIP.664 trimer.

Embodiments of the present disclosure also include a vaccine design process, comprising: administering a proposed vaccine to a test subject; imaging the immune complex formed by an elicited antibody in the test subject upon administration of the proposed vaccine; processing and visualizing the image to determine the likely immunogenicity of the proposed vaccine; and determining that the proposed vaccine is immunogenic if it binds to an antibody and determining that the proposed vaccine should be redesigned if it does not bind or binds weakly to the antibody. In one embodiment, the elicited antibody is a secreted antibody, and/or an antibody from the tissue, secretions or feces of the test subject. In one embodiment, the test subject is a mammal. In one embodiment, the test subject is a rabbit, mouse, rat, cow and/or monkey. In one embodiment, the mouse or rat is a humanized mouse or a humanized rat that have been engineered to produce a B-cell that expresses a single human naïve precursor B-cell receptor or multiple immunoglobulin genes. In one embodiment, the test subject is a human. In one embodiment, the visualization step determines whether a single prime or a second prime is given to a patient.

Other features and advantages of the invention will become apparent from the following detailed description, taken in conjunction with the accompanying drawings, which illustrate, by way of example, various embodiments of the invention.

DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

DETAILED DESCRIPTION

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

Figure 1:
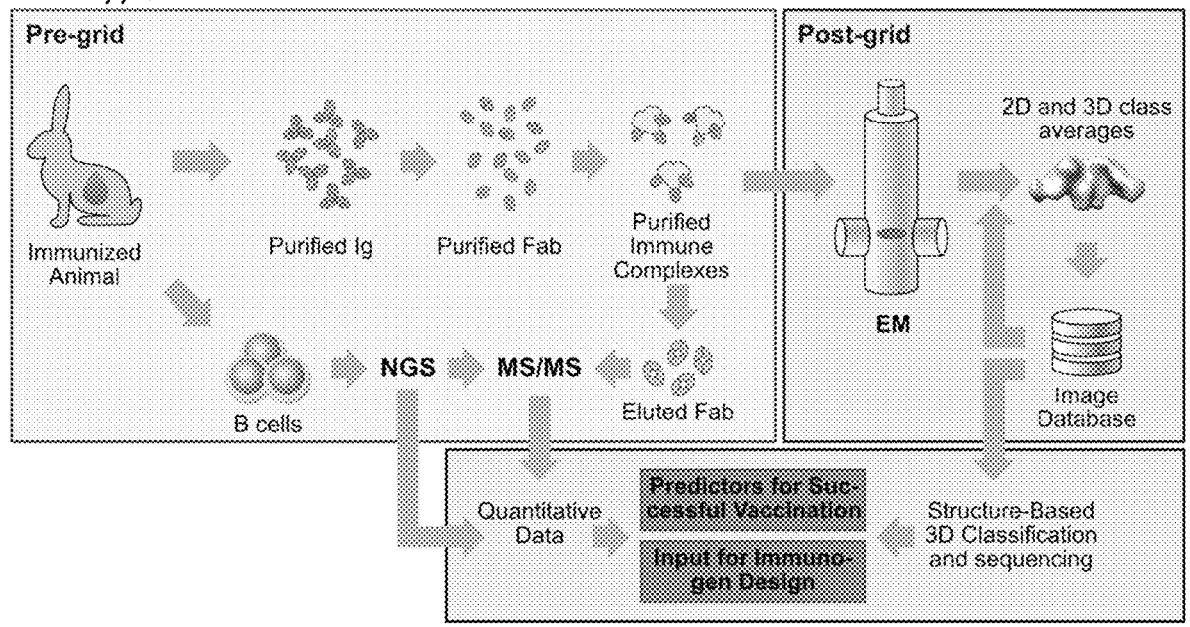
FIG. 1 depicts, in accordance with embodiments herein, workflow for a comprehensive analysis of polyclonal immune responses.

As described herein, in accordance with the various embodiments herein, the inventors have developed a novel method that allows for a comprehensive mapping of the epitopes recognized by polyclonal antibodies elicited by immunizations or infection. The method is based on a workflow that is outlined in FIG. 1 and includes preparation and purification of polyclonal immune complexes, imaging of the complexes, processing of the images including the generation of 2D and 3D class averages and the quantification thereof, and biochemical analysis of the antibodies in the immune complexes by mass spectrometry or mass spectrometry assisted by NGS. The innovation of the method lies in two main areas: first, the ability to form and purify immune complexes for imaging, and second, the development of computation algorithms for interpretation and classification of single particle EM data.

In one embodiment, disclosed herein is a method of mapping immune response to an immunogen, comprising: immunizing a subject with an immunogen and obtaining sera from the immunized subject at multiple time intervals following immunization, wherein the sera comprises one or more immune complexes between the immunogen and serum antibodies, imaging, by electron microscopy, the sera obtained from the immunized subject in each of the time intervals, to obtain structural images of the one or more immune complexes formed between the immunogen and serum antibodies; mapping immune response to the immunogen by measuring differences in structural images obtained at different time intervals to simultaneously visualize diverse antibodies targeting distinct epitopes in the immunized subjects. In one embodiment, disclosed herein is a method for rapid analysis of an immune complex, comprising: providing a polyclonal immunoglobulin purified from immunized or infected subject; preparing fragment antigen binding (Fab) from the polyclonal immunoglobulin; binding the Fab to an immunogen to form the immune complex; purifying the immune complex; and analyzing the immune complex. In one embodiment, the immunoglobulin is IgA (immunoglobin A), IgD (immunoglobin D), IgE (immunoglobin E), IgG (immunoglobin G), IgM (immunoglobin M), or combinations thereof. In one embodiment, the immunoglobulin is purified from the plasma, sera, tissue, secretions or feces of the subject. In one embodiment, the binding step is performed by incubating the Fab and the immunogen together in a solution. In one embodiment, the immune complex is purified by a chromatographic method. In one embodiment, the chromatographic method if size exclusion chromatography (SEC). In one embodiment, the immune complex is analyzed by an imaging method or a spectrometric method. In one embodiment, the imaging method is electron microscopy (EM) or cryoEM. In one embodiment, the immune complex is analyzed by Mass Spectrometry, next generation sequencing (NGS), MS/MS and/or NGS-assisted MS/MS. In one embodiment, the subject is a mammal. In one embodiment, the subject is a human. In one embodiment, the rapid analysis of the immune complex allows for characterization and quantification of antibody responses elicited by immunization or infection. In one embodiment, the method provides real time analysis of ongoing immunization experiments. In one embodiment, the ongoing immunization experiments comprise human vaccine trials. In one embodiment, the method provides cues for the improvement of the immunogen in case of failure of the human vaccine trial. In one embodiment, the immunogen is a recombinant immunogen. In one embodiment, the immunogen is an epitope scaffold and/or an antigen. In one embodiment, the method maps the epitopes recognized by the antibody.

In one embodiment, the present disclosure provides a method comprising: generating an immune complex; imaging the immune complex; processing the images to generate 2D and 3D class averages and quantification thereof; and qualitative and/or quantitative assaying of the immune complex. In one embodiment, the qualitative and/or quantitative assaying of the immune complex is by electron microscopy (ES), mass spectrometry, tandem mass spectrometry, next generation sequencing, or combinations thereof. In one embodiment, the immune complex is a polyclonal immune complex. In one embodiment, the immune complex comprises an antigen-antibody complex. In one embodiment, the method characterizes the epitopes recognized by the antibody in the antigen-antibody complex. In one embodiment, the method further comprises purifying the immune complex prior to the imaging step.

In one embodiment, the present disclosure is towards a method for characterizing epitopes recognized by polyclonal antibodies, comprising: preparation and purification of the polyclonal immune complexes; imaging of the complexes; processing of the images including generation of 2D and 3D class averages and quantification thereof; and qualitative and/or quantitative assaying of the antibodies in the immune complexes by mass spectrometry and/or next generation sequencing (NGS).

In one embodiment, disclosed herein is a method of forming an immune complex comprising: providing an immunoglobulin (Ig) antibody; enzymatically digesting the Ig into fragment antigen binding (Fab) and complexing the Fab with a soluble pathogen and/or antigen; quantifying the specific Ig content for immune complex formation; and forming the immune complex by incubating the pathogen and/or antigen with an excess of Fab. In one embodiment, the enzyme used for digestion is in solution. In one embodiment, the enzyme used for digestion is immobilized on a resin. In one embodiment, the enzymatic digestion is done by a protease. In one embodiment, the Ig is IgA (immunoglobin A), IgD (immunoglobin D), IgE (immunoglobin E), IgG (immunoglobin G), IgM (immunoglobin M), or combinations thereof. In one embodiment, the IgA is enzymatically digested using IgA proteases selected from the group comprising of but not restricted to *Clostridium ramosum, Neisseria gonorrhoeae, Neisseria meningitidis, Haemophilus influenzae,* and *Streptococcus pneumonia,* or combinations thereof. In one embodiment, the IgM is enzymatically digested using suitable proteases comprising but not restricted to Pepsin, Trypsin or species-specific bacterial IgM proteases. In one embodiment, the IgG is enzymatically digested using a suitable proteases comprising but not restricted to papain or ficin. In one embodiment, the proteases are used as soluble enzyme. In one embodiment the proteases are immobilized on an insoluble substrate. In one embodiment, the antigen is an immunogen. In one embodiment, the pathogen and/or antigen is a HIV envelope protein. In one embodiment, the antigen is expressed as BG505 SOSIP trimer.

Figure 2:
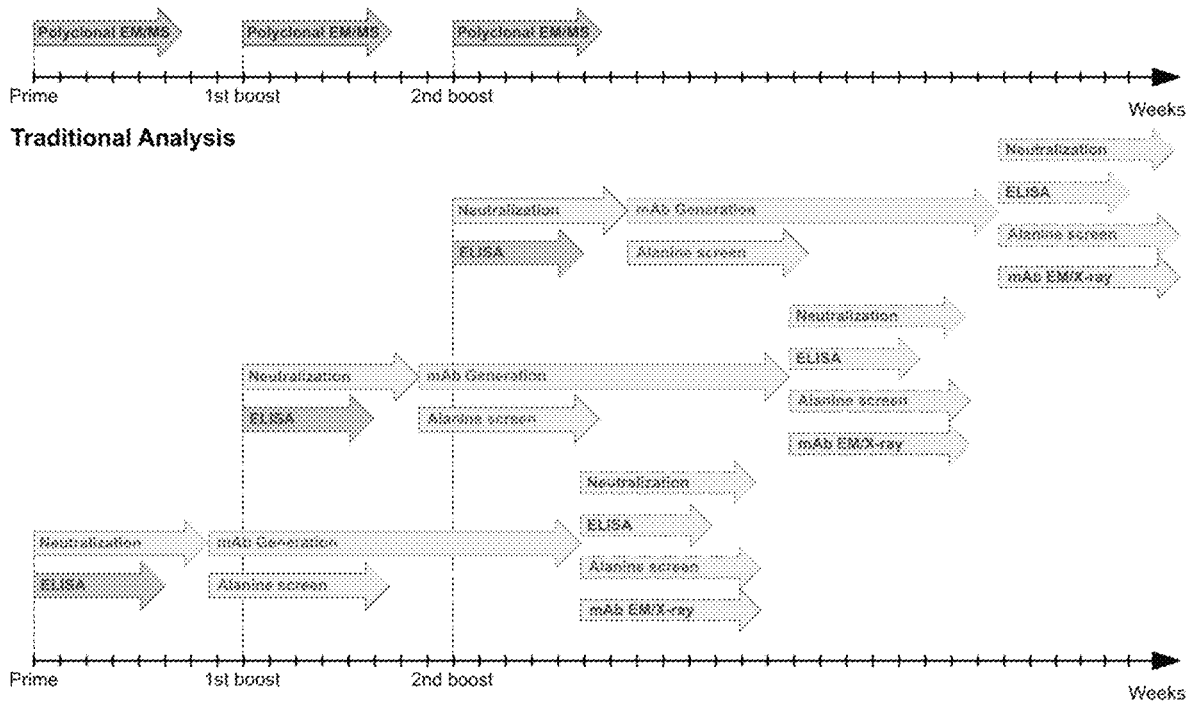
FIG. 2 depicts, in accordance with embodiments herein, advantages of the instantly disclosed methods compared to traditional approaches.

Currently, the only way of characterizing humoral immune responses include the use of competitive ELISA, loss of binding or neutralization variants of the antigen, serially overlapping peptides (PepScan), deep sequencing, and the preparation and characterization of monoclonal antibodies (FIG. 2). These methods are very tedious and time consuming and only provide a rough estimate of the specificities of the elicited antibodies. While the structure of a monoclonal antibody in complex with its antigen provides for a more complete description, generation of monoclonal antibodies is tedious and time consuming and only allows the processing of very limited number of samples. Consequently, detailed analyses of the epitopes targets and progression of antibody responses are only available after the immunization study has been completed. Further analyses also only focus on antibodies with a biological function (example, neutralization) and leaves the remainder of the humoral immune response uncharted. Due to the high cost and labor involved, unsuccessful vaccination experiments are hardly ever analyzed in detail, and the reasons for the failure of a given immunogen typically takes months, if not years, and thus comprises a serious rate limiting step in the investigation of humoral immune responses and vaccine development.

In one embodiment, the methods disclosed herein allows for a rapid characterization and quantification of antibody responses elicited by immunization or infection, including comprehensive analyses of numerous samples within weeks to a month, and thus is suitable to provide real time analysis of ongoing immunization experiments, which typically have an interval of 4-8 weeks between priming and boosting. In one embodiment, the methods disclosed herein would be suitable to perform real time monitoring of human vaccine trials to identify correlates of protection, wherein the term real time monitoring refers to monitoring within 2-4 days, or within one week. In case of failure of a vaccine candidate, it would provide important clues for the improvement of the immunogen. During iterative vaccine development strategies, such as structure-guided immunogen design, the instant method enables the rapid evaluation of an immunogen candidate and provides specific feedback for selection or improvement of subsequent booster immunogens. Moreover, by coupling electron microscopy to mass spectrometry, a comprehensive and quantitative analysis can be obtained.

In one embodiment, disclosed herein is a vaccine design process, comprising: administering a proposed vaccine to a test subject; imaging the immune complex formed by an elicited antibody in the test subject upon administration of the proposed vaccine; processing and visualizing the image to determine the likely immunogenicity of the proposed vaccine; and determining that the proposed vaccine is immunogenic if it binds to an antibody and determining that the proposed vaccine should be redesigned if it does not bind or binds weakly to the antibody. In one embodiment, the elicited antibody is a secreted antibody, and/or an antibody from the tissue or feces of the test subject. In one embodiment, the test subject is a mammal. In one embodiment, the test subject is a rabbit, mouse, rat, dog, cow, pig and/or monkey. In one embodiment, the mouse or rat is a humanized mouse or a humanized rat that express human naïve precursors. In one embodiment, the test subject is a human. In one embodiment, the visualization step determines whether a single prime or a second prime is given to a patient.

Embodiments of the present disclosure are further described in the following examples. The examples are merely illustrative and do not in any way limit the scope of the invention as claimed.

EXAMPLES

Example 1

Generally

Polyclonal humoral immune responses, for example to natural infection and vaccination, are inherently complex and difficult to characterize using currently available methodologies. Mapping of all epitopes in an immune response is typically incomplete and, therefore, creates a barrier to fully understand the humoral response to infection and hence can hinder rational vaccine design efforts. The present disclosure provides a new methodology that the inventors have applied to characterize polyclonal responses in rabbits to immunization with a trimeric HIV-1 envelope glycoprotein subunit vaccine candidate, BG505 SOSIP.664, using single particle electron microscopy. This approach was able to detect known epitopes and reveal how antibody responses evolved during the prime-boost-boost-boost strategy that ultimately resulted in a neutralizing antibody response. Furthermore, previously unknown epitopes were uncovered, including non-neutralizing epitopes, as well as an epitope in the proximity of one recognized by human broadly neutralizing antibody responses. The method described provides a rapid, relatively complete and semi-quantitative map of epitopes targeted in a polyclonal antibody response and should be of widespread utility in vaccine and infection studies.

Classically, vaccines are comprised of killed or attenuated pathogens, or protein subunits derived from the pathogen surface. Although most successful vaccines on the market are based on these approaches, highly antigenically variable pathogens, such as HIV, and pathogens that circulate in the population as a large number of serotypes, have proven less tractable. A different approach based on isolating functional antibodies to the pathogen, studying their interaction with their targets, and then designing vaccine candidates has been described. For highly antigenically variable pathogens, broadly neutralizing antibodies (bnAbs), i.e. antibodies that can recognize multiple antigenic variants thereof, can be isolated only from a small subset of infected patients. The target for HIV bnAbs is a metastable structure on the surface of the viral particle consisting of two glycoproteins gp120 and gp41 that are arranged in a $(gp120)_3(gp41)_3$ trimeric assembly. Stabilization is required for the generation of a recombinant molecule (SOSIP) that mimics the native trimer on the virus and these recombinant trimers are bound well by bnAbs. However, the inferred germline versions of bnAbs typically fail to recognize both the recombinant trimers and the corresponding viral envelope but engineered proteins have been generated to stimulate precursor B cells of bnAbs and help advance structure-guided vaccine development against HIV based on the use of sequential immunogens.

Although the first immunization experiments using native recombinant envelope trimers and germline targeting immunogens in diverse animal models look promising and were able to elicit tier 2 autologous neutralizing antibodies, one of the rate-limiting steps in the iterative vaccine development approach is in analysis of the polyclonal immune response elicited by immunization. Serum neutralization assays and enzyme-linked immunosorbent assays (ELISA) are typically used as reasonably rapid readouts of the epitopes recognized by elicited antibodies. However, to gain a more detailed picture requires the generation of monoclonal antibodies, and determination of their structures in complex with immunogen. This process is time consuming and limited to a relatively small number of samples. Such analyses typically focus on antibodies with a biological function (e.g. neutralization) and often leave the remainder of the humoral immune response less well investigated. Due to the high cost and labor involved, unsuccessful outcomes of vaccination experiments are hardly ever analyzed in detail, and the reasons for failure of a given immunogen to generate neutralizing response can remain unknown. More recent efforts to use deep sequencing of the B cell receptor (BCR)

repertoire of responding B cells have considerable limitations, because in most cases, the heavy-light chain pairing is lost. Next generation sequencing (NGS) analyses can be used to study responses but require a considerable amount of pre-existing knowledge to interpret the sequencing data: unless characteristic features of bnAb sequences are known, or a comprehensive reference database of previously isolated and sequenced pathogen-specific B cell clones or mAbs is available, these analyses have to rely on identifying changes in the frequencies of V region clonotypes or families compared to the pre-immune state. Approaches that couple NGS data with tandem mass spectrometry (MS/MS) analyses of affinity purified antibodies enabled the identification of B cell receptor sequences that are antigen-specific without prior knowledge of their genetic signatures. These novel approaches have brought interesting and more comprehensive insights into B cell responses; however, they cannot provide direct information about the epitope recognized unless the sequenced BCR sequences are synthesized and expressed as antibodies to be validated and gain insight into their specificity.

HIV trimer BG505 SOSIP.664 immunization of rabbits has previously been used to determine the immunogenicity of recombinant native envelope trimers. These prior studies employed intramuscular prime immunization with 30 g of BG505 SOSIP.664 with Iscomatrix adjuvant at day 0 followed by booster immunization using the same formulation at weeks 4 and 24. It was found that BG505 SOSIP.664 immunization can induce autologous Tier 2 neutralizing antibody titers. Neutralizing monoclonal antibodies 10A, 11A, and 11B isolated from BG505 SOSIP.664 immunized rabbits led to the definition of a highly immunogenic glycan hole present in the envelope of the BG505 Env in the vicinity of N241. Antibodies specific for this particular epitope were identified as the primary source of neutralization and, using negative stain electron microscopy (nsEM), were shown to approach the Env surface from the membrane-proximal side of the trimer. Besides this class of Tier 2 neutralizing antibodies, two Tier 1 neutralizing antibodies were identified: 10B recognizing the V3-loop and 10C that was found to compete with CD4 binding site-specific bnAbs on gp120 but bound poorly to envelope trimers. Last, 12A-like antibodies that displayed weak autologous neutralizing activity but bound to a different epitope than 10A, 11A, and 11B were identified. 12A-mediated neutralization was impaired in the presence of a glycan at position 611. nsEM revealed that mAb 12A bound to an epitope in the vicinity of the PGT151 epitope and at a more canonical bnAb angle of approach than 10A, 11A and 11B. These studies offer important information about the diversity of humoral immune responses, including non-neutralizing epitopes. Here a complementary approach is described that elucidates the total landscape of the antibody response, including the genesis and evolution of antibody responses targeting different epitopes on Env. These data, that can be rapidly generated, can inform the iterative, structure-based vaccine design process.

Example 2

BG505 SOSIP.664 Immunization

Figure 3:
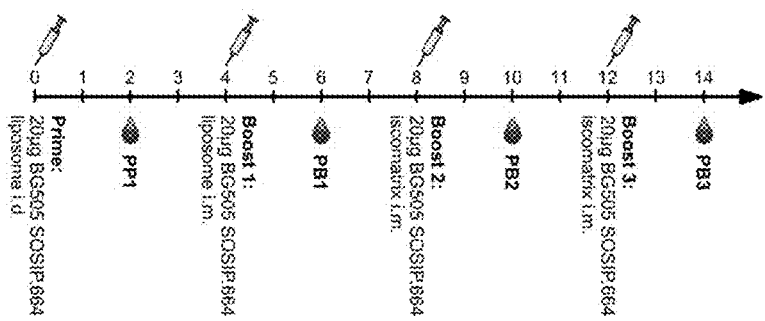
FIG. 3 depicts, in accordance with embodiments herein, epitope mapping of the antibody response to BG505 SOSIP.664 trimers in rabbits by negative stain electron microscopy (nsEM). (A) Immunization schedule. (B) Representative reference-free 2D class averages obtained after each BG505 SOSIP.664 immunization of rabbit 3417. Fabs are highlighted in false colors: red for bottom binding (BOT), blue for glycan hole (GH), and orange for cleft-of-trimer (COT). (C) 3D reconstructions of the four basic antibody classes elicited by BG505 SOSIP.664 immunization of rabbits. Side and top view are shown for representative 3D reconstructions and 2D class averages. Densities for mAbs 10A and PGT151 are added as semitransparent references in the GH2 and COT 3D reconstructions, respectively. BOT-, GH-, and COT-specific antibodies are highlighted with false colors red, blue and orange, respectively. Representative 2D class averages are shown below each view, where available. A comparison of the two GH classes and variations of the BOT epitope recognition is depicted in a box on the right side.
Figure 3:
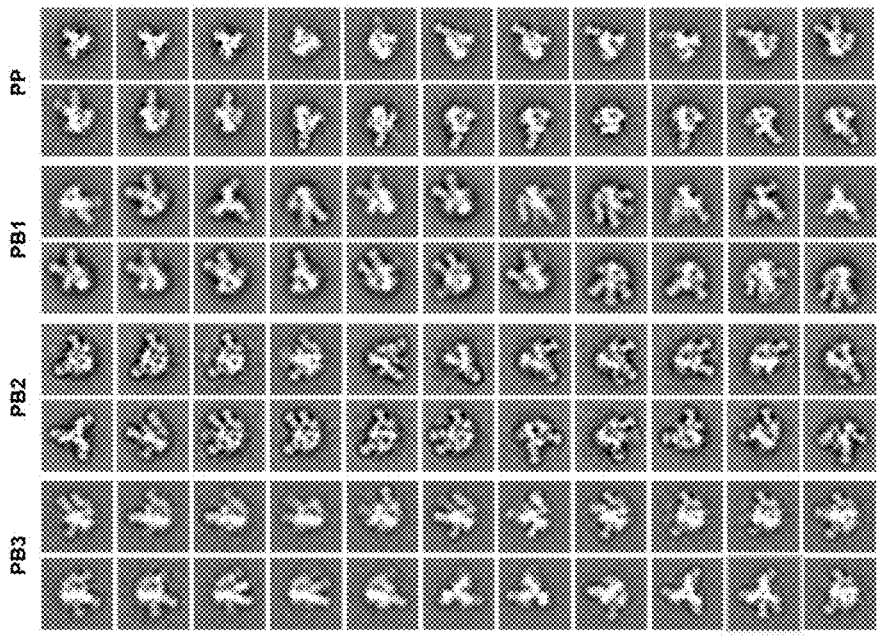
Figure 3:
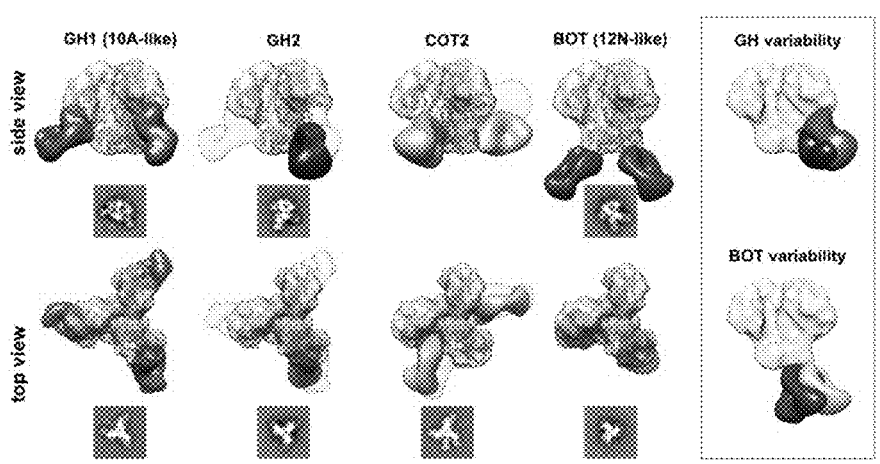
Figure 9:
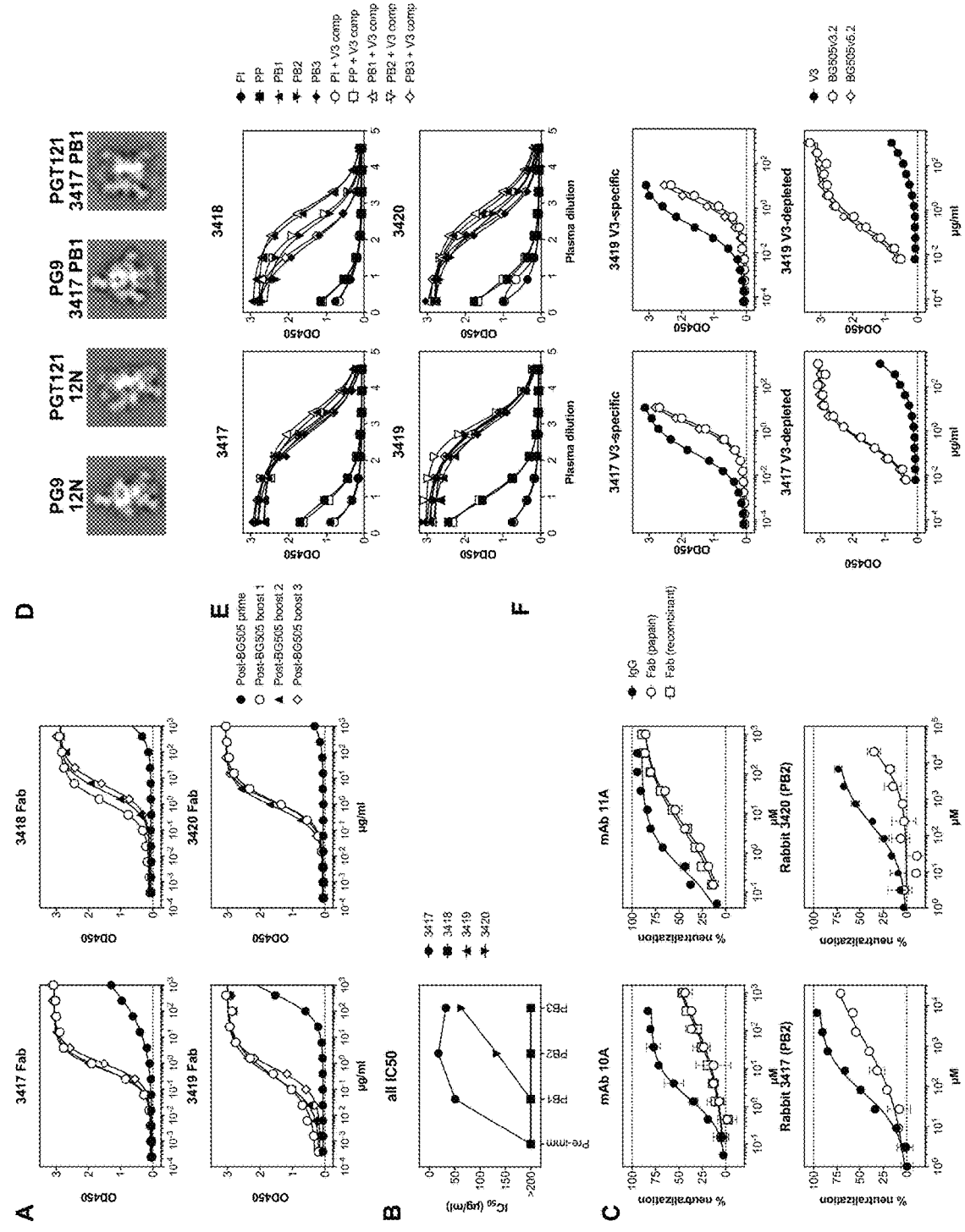
FIG. 9 depicts, in accordance with embodiments herein, ELISA and autologous neutralizing titers of polyclonal Fabs prepared from rabbits 3417-3420. (A) Recombinant biotinylated BG505 SOSIP.664 was captured on neutravidin-coated ELISA plates before serial dilutions of rabbit Fabs were added. Fab binding was measured with an HRP-conjugated secondary anti-rabbit F(ab')$_2$-specific antibody. (B) Autologous neutralizing antibody titers in purified IgG isolated from immunized rabbits. Serially diluted IgGs were first incubated with BG505 N332 pseudovirus and then infection assessed on TZM-bl cells by luciferase measurement. (C) Impact of enzymatic digestion and valency on neutralizing activity against BG505 N332. (Upper panels) Fabs of mAb 10A and 11A were either generated by digestion with papain or by recombinant expression in 293F cells. The neutralizing activity of the purified Fabs was then compared to the corresponding activity of the full IgG molecule as described above. (Lower panels) As above but using purified serum IgG or papain-digested Fabs prepared from serum of the indicated rabbits at PB2. (D) 2D class averages of complexes formed between the indicated mixes of mAb PG9, PGT121 and 12N, as well as with polyclonal Fabs from 3417 PB1. Fab densities are highlighted in false colors: blue for GH1, red for BOT, green for PG9 and purple for PGT121. (E) BG505 V3-competition ELISA. Performed as described above but incubating the rabbit plasma dilutions with 150 µg/ml BG505 V3-peptide before adding them to the BG505 SOSIP.664-coated ELISA plates. (F) Detection of V3-specific Fabs in BG505 SOSIP.664-immunized rabbits. V3-specific Fabs were affinity-purified using biotinylated BG505 V3-peptide immobilized on streptavidin-agarose. Binding of the eluted Fabs (top panels) and the corresponding V3-depleted Fabs (bottom panels) to the V3-peptide or BG505 SOSIP.664 trimers was evaluated by ELISA as described above.

In one embodiment, sera from four BG505 SOSIP.664 immunized rabbits were used, that have been extensively characterized and disclosed by the authors in McCoy et al, Cell Rep. 2016 Aug. 30; 16(9): 2327-2338, and that are referred to as 3417, 3418, 3419, and 3420. Rabbits were immunized three times with BG505 SOSIP.664 and bled two weeks following each immunization (FIG. 3A). Sera obtained are referred to as PP, PB1, PB2, and PB3 for post prime, post boost 1, post boost 2 and post boost 3, respectively. Characterization of the sera using ELISA (FIGS. 9A and 9E) and neutralization assays (FIG. 9B) demonstrated that the antibody responses were comparable to those previously published. As in previous studies, only low titers of binding antibodies were induced following the prime (FIGS. 9A and 9E). The first booster immunization of this immunization regimen drastically increased these binding antibody titers to nearly maximum levels, with little further improvement afforded by subsequent immunizations. No autologous neutralizing antibodies were induced by the priming immunization and neither rabbit 3418 nor 3419 developed neutralizing antibody titers above detection level during the entire course of immunizations (FIG. 9B). In the other two rabbits following the first boost, neutralizing titers substantially increased in rabbit 3417 but not in rabbit 3420 where neutralizing titers were only observed after the second boost. The third booster did not to improve the already high neutralizing antibody titers in rabbit 3417 and even resulted in slightly lower titers compared to PB2 (FIG. 9B). In the slower responding rabbit 3420, the third immunization improved its neutralizing titers to around half the titer observed in rabbit 3417 (i.e. IC50 63 µg/ml vs 32 µg/ml). As would be known to a skilled artisan in the art, while the inventors have used the BG505 antigen in their experiments to illustrate the methods disclosed herein, other antigens or envelope trimer variants may be used in a similar manner to practice the methods and concepts disclosed herein.

Example 3

Polyclonal Antibody Characterization

To determine the epitopes of the elicited antibodies without generation of monoclonal antibodies, the inventors devised a strategy to directly image immune complexes formed between the immunogen (BG505 SOSIP.664) and the induced serum antibodies by nsEM. Serum immunoglobulin G (IgG) was purified using a mixture of protein A and G affinity matrix, and processed into fragments antigen binding (Fabs) using immobilized papain to prevent antigen crosslinking and aggregation due to the bivalent nature of IgG. Before nsEM, Fabs were subjected to extensive biochemical and antigenic characterization. Purity of the Fabs was confirmed by SDS PAGE and size exclusion chromatography (SEC). To investigate the effect of the IgG digestion protocol on the biological activity of antibodies, neutralizing titers to the immunogen before and after IgG digestion were determined. As depicted in FIG. 9C, a considerable reduction of neutralizing activity was observed for the polyclonal serum when digested into Fabs. However, since monoclonal antibodies (mAbs) 10A and 11A also displayed a comparable loss in neutralizing activity when recombinantly expressed as Fabs, it was conclude that proteolytic digestion did not have gross detrimental effects beyond those associated with reducing binding valency and molecular size of the antibodies.

Example 4

Polyclonal Image Analysis

For the purposes of the current study, the sera of rabbits 3417, 3418, 3419, and 3420 were imaged. Due to the limited amount of serum available, and the low titers following the prime vaccination (FIGS. 9A and 9E), PP complexes could only be identified for rabbit 3417. Complexes were purified via size exclusion chromatography and deposited onto an EM grid and imaged. For each sample, 10,000-50,000 individual particle images were collected that were submitted to reference-free 2D classification (FIG. 3B). Interestingly, following priming, the early antibody response was completely dominated by bottom of trimer (BOT)-binding antibodies. Notably, these antibodies bind to a neo-epitope unique to the soluble Env trimer that does not exist on membrane-embedded Env. Hence, for the most part, these correspond to non-neutralizing responses. After the first booster immunization, antibodies to the glycan hole (GH) epitope were also identified in rabbits that developed neutralizing titers (3417 and 3420), but not in rabbits that did not mount neutralizing titers (3418 and 3419).

Figure 10:
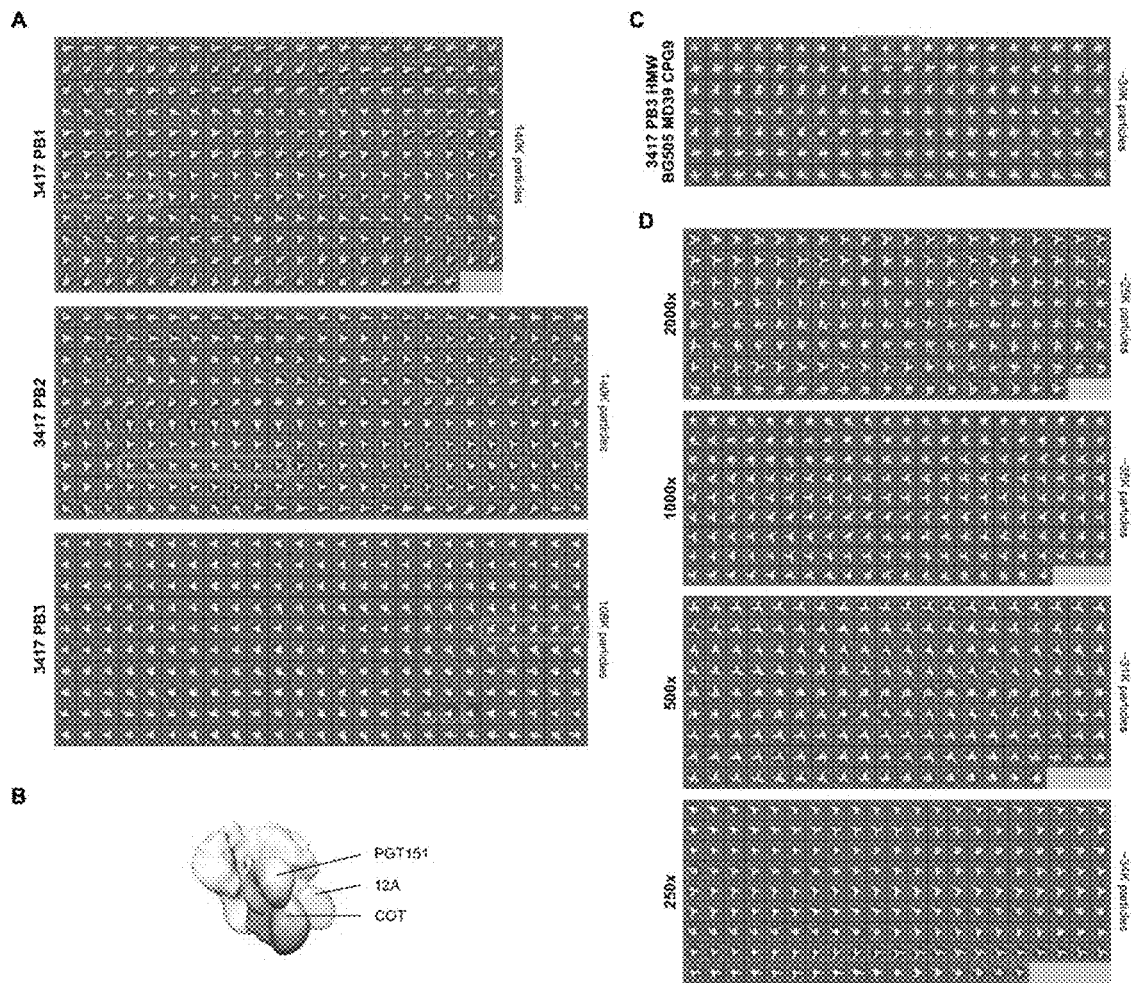
FIG. 10 depicts, in accordance with embodiments herein, (A) Increased detection of COT antibodies in immune complexes formed with a variant of BG505 SOSIP.664 in which the GH1 epitope was eliminated by the addition of N-linked glycosylation sites at positions 241 and 289 of gp120. 2D class averages with clearly visible COT antibodies are highlighted with orange boxes. The number of total particles used for 2D class averaging is indicated on the right. (B) Comparison of nsEM densities of antibodies binding to the fusion peptide region. Densities of COT-class Fabs, and Fabs of monoclonal antibodies PGT151 (EMDB 5918) and 12A are depicted, as indicated. (C) Increased detection of COT-class antibodies when both the glycan-hole and the BOT epitopes are silenced. Reference-free 2D class average of immune complexes formed between BG505 MD39 CPG9 and 3417 PB3 Fabs. The number of total particles used for 2D class averaging is indicated on the right, 2D-class averages showing occupancy of 3 COT Fabs are boxed. (D) Immune complexes formed with titrated amounts of 3417 PB2 Fab. Two-fold titrated amounts of 3417 PB2 Fab fragments, starting at 2000×$EC_{50}$ concentration, and a constant amount of BG505 SOSIP.664 was used for complex formation and nsEM. Reference-free 2D class averages are depicted with the number of particles averaged indicated on the right side.

3D refinement was performed that yielded 3D classes representing the most predominant immune complexes for all rabbits. When all reconstructions were overlaid, and compared to prototypic mAbs, two GH-specific, one BOT and one cleft-of-trimer (COT) binding classes could be defined (FIG. 3C). BOT antibodies recognize an epitope similar to the previously described bottom-binding mAb 12N, and were, therefore, binned into one class, although some variation in epitope and angle of approach was detectable in the 3D reconstructions (FIG. 3C, box). Glycan hole 1 (GH1) class antibodies almost perfectly overlap with 10A, a prototypic glycan hole-specific neutralizing mAb described earlier in McCoy et al, Cell Rep. 2016 Aug. 30; 16(9): 2327-2338. Relative to 10A, the second GH-specific class, GH2, binds in an orientation rotated approximately 90° along its longitudinal axis to the same region. COT class antibodies, i.e. antibodies that bind between the trimer blades, were rarer, but could be detected in all bleeds after PB1 in the 2D class averages (FIG. 10A), but not in the 3D classes. COT class antibodies were found to bind membrane-proximal, thus below fusion peptide-specific antibodies such as PGT151. This region, typically referred to as the gp120-gp41 interface, is actually a cluster of overlapping epitopes that includes COT, PGT151, and the previously described rabbit mAb, 12A, which preferentially neutralizes viruses lacking the glycan at N611 (FIG. 10B).

In one embodiment, the inventors determined that the relative dominance of the BOT and GH antibodies prevented detection of COT antibodies in the 3D classes. Hence the original BG505 SOSIP.664 probe was not sensitive enough to completely characterize the polyclonal response. When complexes were instead formed with Env trimers in which either the glycan hole alone or the glycan hole and the bottom were modified to diminish antibody binding, the frequency of detection of COT antibodies increased considerably in 2D class averages, and 3D models could be generated from such immune complexes (FIG. 10C). In contrast to human bnAb PGT151, that binds with a stoichiometry of 2 Fabs per trimer, COT class antibodies were found to bind with up to 3 molecules per trimer (FIG. 10C, box). GH- and COT-specific antibodies could be concomitantly bound to the same cleft of the trimer (cf. FIG. 3B, box), indicating that there is no direct steric hindrance between the two classes.

Figure 4:
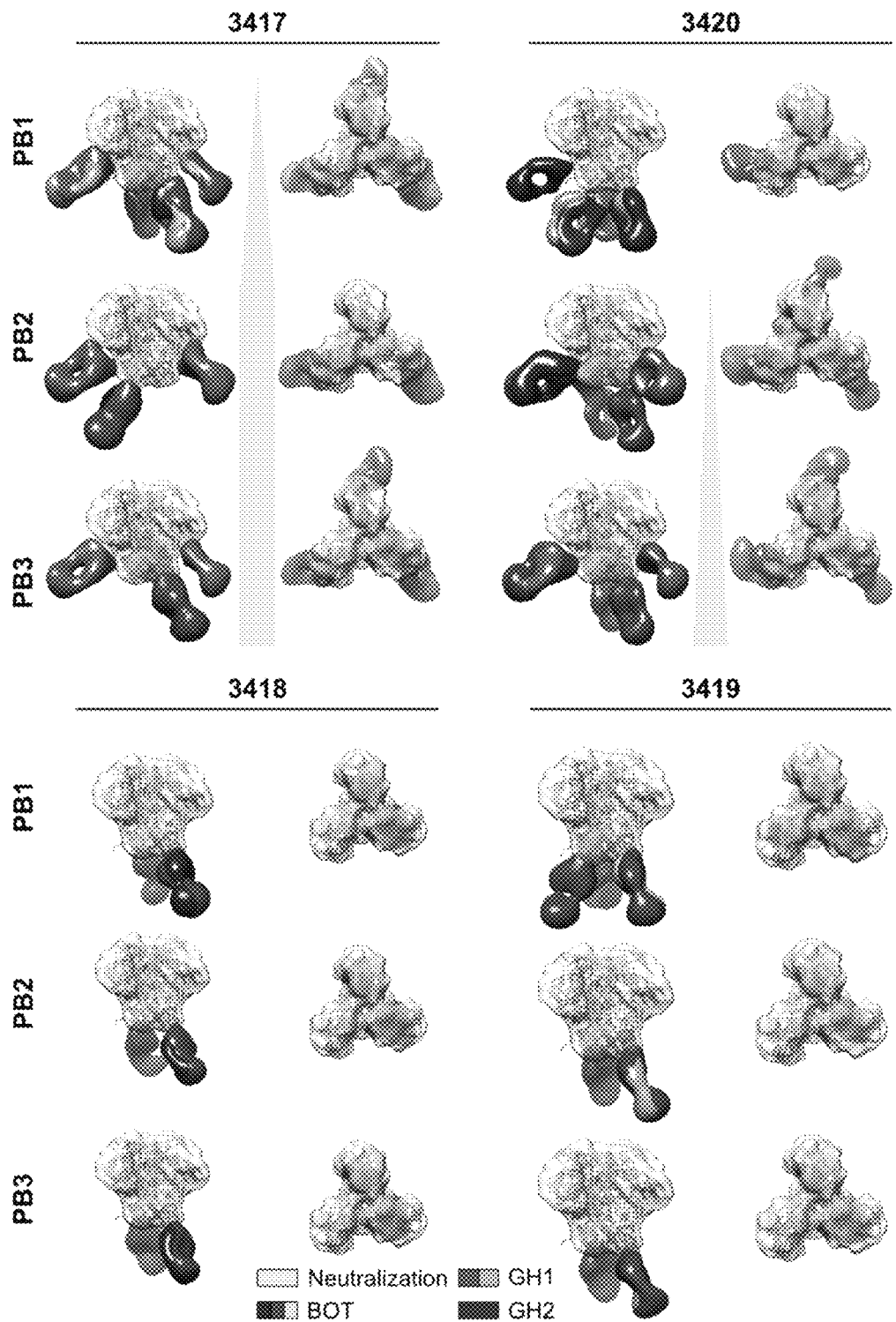
FIG. 4 depicts, in accordance with embodiments herein, epitope mapping of the antibody responses in the 4 rabbits at different time points during the immunization schedule. Refined 3D models were fitted onto a low pass filtered envelope trimer reference structure (PDB 518H, displayed as ribbons with gp120 in bright blue and gp41 in dark gray). Densities corresponding to Fabs were separated and colored. For display of the surface, the density map for fully glycosylated BG505 SOSIP.664 (EMDB 5782) was aligned as described above and displayed in semitransparent gray. Side and top views are displayed. A bright green wedge (between side and top views) illustrates the development of autologous neutralizing titers in two of the rabbits.

BOT-specific antibodies were the first and only class of antibodies detectable after priming (FIG. 3B) and remained detectable throughout the course of immunization in all rabbits (FIG. 4). In the two rabbits that developed autologous neutralizing titers (3417 and 3420), the differences in the kinetics of the development of neutralizing titers was also reflected in the classes of antibodies found. In the rapidly responding rabbit 3417, the appearance of GH1 antibodies coincided with the development of neutralizing titers at PB1, and GH1 remained the only GH-binding class of antibodies. In contrast, in the slowly responding rabbit 3420, GH2 but no GH1 class antibodies were detectable at PB1 (FIG. 4). As no neutralizing activity was found in this rabbit at PB1 (FIG. 9B), it suggests that the GH2 class of antibodies did not confer substantial neutralization activity against BG505. However, when autologous neutralizing activity became detectable in rabbit 3420 after PB2, GH1 antibodies became readily identifiable in the 3D reconstructions (FIG. 4). This suggests that GH1 class antibodies, like mAb 10A, are predominantly responsible for the neutralizing activity in these BG505 SOSIP.664 immunized rabbits.

To independently confirm the findings made by nsEM, the inventors used SEC to compare Fab occupancy in complexes formed with wt BG505 SOSIP.664 and a variant thereof, in which mutations S241N and P291S were made to introduce N-linked glycosylation sites at positions N241 and N289. The 241 or 241/289 mutations have previously been shown to knock out the neutralizing antibody response, consistent with structural observations.

Figure 5:
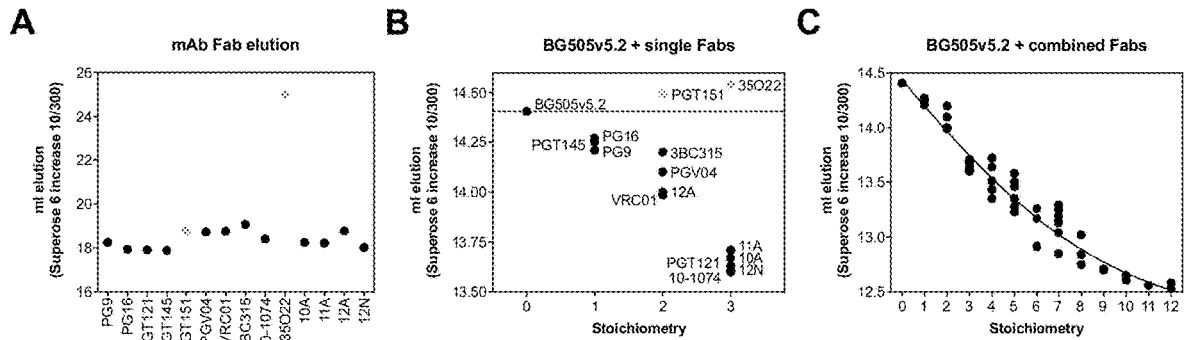
FIG. 5 depicts, in accordance with embodiments herein, generation of a standard curve for measuring Fab occupancy in immune complexes. (A) Elution volumes of Fabs purified from the indicated mAbs. (B) Elution volumes of immune complexes saturated with a single Fab specificity or (C) combined Fab specificities to determine a standard curve for the calculation of Fab occupancy in immune complexes. Note that complexes containing PGT151 and 35022 were excluded from the right panel due to their aberrant elution behavior.

To determine the Fab occupancy in immune complexes, a panel of well-characterized mAbs was digested into Fabs, and their molecular weight estimated by measuring retention volume by SEC. Most free Fabs eluted at around 18 ml from a Sepharose 6 increase 10/300 column (FIG. 5A). When immune complexes were formed between BG505 SOSIP.664 and saturating concentrations of a single Fab specificity, their previously determined stoichiometry of binding was reflected in their elution volume (FIG. 5B). However, complexes containing 35022 or PGT151 Fabs were retained considerably longer than expected and were, therefore, excluded from further analysis. Finally, a large number of distinct immune complexes was formed that combined mAbs of different binding stoichiometries, and their elution volumes were determined (Table 1). These data enabled us to calculate a standard curve for estimating Fab occupancy directly from the elution volume of an immune complex (FIG. 5C). To correct for the different amounts and affinities of BG505-specific antibodies present in the Fab preparation from the different bleeds, $EC_{50}$ values were determined by ELISA (FIGS. 6A and 9), and standardized immune complex formation was performed by overnight incubation of 10-25 μg of BG505 SOSIP.664, or variants thereof, with 2000× the $EC_{50}$ concentration of Fabs determined by ELISA. Complexes were subjected to SEC to remove non-bound Fabs and estimate the average stoichiometry of Fabs bound to the immunogen. After SEC elution, complexes were subjected to single particle nsEM.

TABLE 1

Calculated mAb occupancy and elution volumes for immune complexes formed with saturating concentrations of the indicated mAbs. Complexes containing 35O22 and PGT151 (italicized) were excluded from the analysis due to abnormal behavior on SEC. Fab 35O22 displayed a considerably prolonged retention in SEC (probably due to stickiness to the matrix). Excessive proteolytic degradation did not account for this observation as the Fab displayed the expected molecular weight in SDS PAGE (not shown). Thus, it is likely that 35O22 non-specifically interacts with the SEC matrix. Moreover, complexes only containing 35O22 or PGT151 Fabs ran at a molecular weight even smaller than uncomplexed BG505 SOSIP.664.

| Complex composition | Calculated mAb occupancy | Elution volume |
| --- | --- | --- |
| No antibody (BG505 SOSIP.664 only) | 0 | 14.33 |
| PG9 | 1 | 14.21 |
| PG16 | 1 | 14.27 |
| PGT121 | 3 | 13.63 |
| PGT145 | 1 | 14.25 |
| *PGT151* | *2* | *14.5* |
| PGV04 | 2 | 14.1 |
| VRC01 | 2 | 14 |
| 3BC315 | 2 | 14.2 |
| 10-1074 | 3 | 13.6 |
| *35O22* | *3* | *14.54* |
| 10A | 3 | 13.67 |
| 11A | 3 | 13.71 |
| 12A | 2 | 14 |
| 12N | 3 | 13.61 |
| PG9 + VRC01 | 3 | 13.68 |
| PG16 + 10A | 4 | 13.43 |
| PGT145 + PGT121 | 4 | 13.51 |
| *PGT121 + PGT151* | *5* | *13.54* |
| VRC01 + 12A | 4 | 13.63 |
| VRC01 + 3BC315 | 4 | 13.72 |
| PGT121 + VRC01 | 5 | 13.35 |
| 10-1074 + 10A | 6 | 12.91 |
| PGT145 + VRC01 + 12A | 5 | 13.46 |
| PG9 + PGV04 + 3BC315 | 5 | 13.58 |
| PG16 + VRC01 + 10A | 6 | 13.17 |
| *PGT121 + VRC01 + PGT151* | *7* | *13.36* |
| PGT121 + VRC01 + 12A | 7 | 13.14 |
| 10-1074 + PGV04 + 12A | 7 | 13.19 |
| PGT121 + PGV04 + 3BC315 | 7 | 13.29 |
| 10-1074 + PGV04 + 3BC315 | 7 | 13.25 |
| PGT121 + VRC01 + 10A | 8 | 12.84 |
| 12N | 3 | 13.61 |
| 12N + PG9 | 4 | 13.35 |
| *12N + PGT151* | *5* | *13.65* |
| 12N + 12A | 5 | 13.5 |
| 12N + PGT121 | 6 | 12.92 |
| 12N + VRC01 | 5 | 13.23 |
| 12N + 10A | 6 | 13.26 |
| 12N + PG9 + PGT121 | 7 | 12.85 |
| 12N + PG9 + 10A | 7 | 13.04 |
| *12N + PGT121 + PGT151* | *8* | *12.93* |
| 12N + PGT121 + VRC01 | 8 | 12.75 |
| 12N + PGT121 + 10A | 9 | 12.71 |
| 12N + VRC01 + 10A | 8 | 13.02 |
| 12N + PG9 + PGT121 + VRC01 | 9 | 12.7 |
| 12N + PG9 + PGT121 + 10A | 10 | 12.61 |
| 12N + PGT121 + VRC01 + 10A | 11 | 12.56 |
| 12N + PG9 + PGT121 + VRC01 + 10A | 12 | 12.53 |
| PG9 + PGT121 | 4 | 13.51 |
| VRC01 + 10A | 5 | 13.28 |
| 12N + PGT145 + PGT121 | 7 | 12.85 |
| PGT121 + VRC01 + 12A | 7 | 13.13 |
| 12N + PGT145 + PGT121 + 10A | 10 | 12.65 |
| 12N + PGT145 + PGT121 + VRC01 + 10A | 12 | 12.58 |

Figure 6:
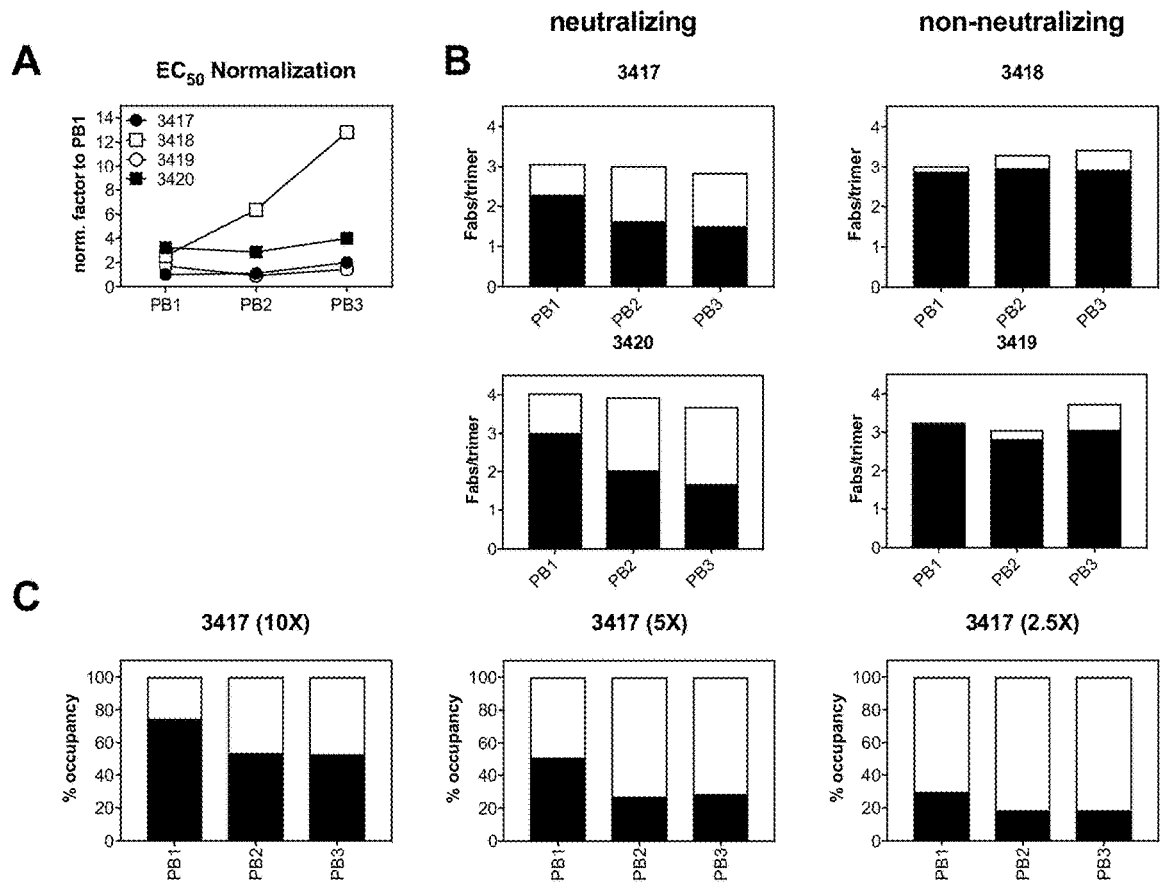
FIG. 6 depicts, in accordance with embodiments herein, analysis of antibody responses to the 241/289 glycan hole by comparison of Fab occupancy of immune complexes formed with BG505 SOSIP.664 with or without the glycan hole. (A) Factors used for normalization to rabbit 3417 PB1 $EC_{50}$ determined by ELISA. (B) Occupancy of GH- (white) and non-GH (black) specific antibodies in immune complexes normalized to PB1-$EC_{50}$ of rabbit 3417. (C) Comparison of relative affinities of GH- (white) and non-GH- (black) specific antibodies determined by measuring Fab occupancy in complexes formed with titrated amounts of rabbit 3417 Fabs.

To assess the occupancy, immune complexes with Fab concentrations standardized to 2000×EC$_{50}$ of 3417 PB1 were formed using BG505 SOSIP.664 and the glycan-restored trimer (FIG. 6). In rabbits that developed neutralization, the fraction of N241/N289-sensitive antibodies (i.e. GH-specific) increased with each booster immunization (3417 and 3420; FIG. 6B). By contrast, in rabbits that failed to mount neutralizing antibodies (3418 and 3419), the antibody response was almost completely independent of the presence or absence of glycosylation at position 241/289, consistent with the nsEM findings.

To compare the overall avidities of the bound antibody classes, titrated Fabs from rabbit 3417 PB1 were used to form complexes with a fixed amount of wt BG505 SOSIP.664 or glycan hole-filled trimer (FIG. 6C). The fraction of glycan hole-indifferent antibodies in the immune complexes decreased with each antibody dilution, indicating that these were of lower abundance or weaker affinity. Again, nsEM imaging of these complexes was consistent with these findings (2D classes for rabbit 3417 PB2 are shown as an example in FIG. 10B).

To assess whether the lack of detection of V3 supersite or apex-specific antibodies was due to perturbation of these epitopes by binding of the predominant BOT or GH antibodies, immune complexes were formed using a mixture of the BOT mAb, 12N, with either PG9 or PGT121, and found that binding of 12N did not affect binding of the other two monoclonal antibodies in nsEM. Likewise, mixing of 3417 PB1 Fabs containing BOT, COT and GH antibodies with either PG9 or PGT121 did not prevent binding of either monoclonal antibody, as determined by nsEM (FIG. 9D). Finally, to determine whether the sera contained V3 loop-specific antibodies, two experiments were performed. First, competition-ELISA using peptides corresponding to the V3-loop of BG505 SOSIP.664 were performed. As no competition was detectable (FIG. 9E), it can be concluded that only a minor fraction of Env-specific antibodies was in fact against the V3 loop. Therefore, V3-specific antibodies were enriched by affinity chromatography and obtained ~1 µg of V3-specific Fabs per mg of total Fabs. A fraction of these V3-specific Fabs were indeed able to bind immobilized BG505 SOSIP.664 in ELISA (FIG. 9F), but were not observed in nsEM, likely due to poor affinity and fast off-rates.

Example 5

3D cryoEM Studies

Figure 7:
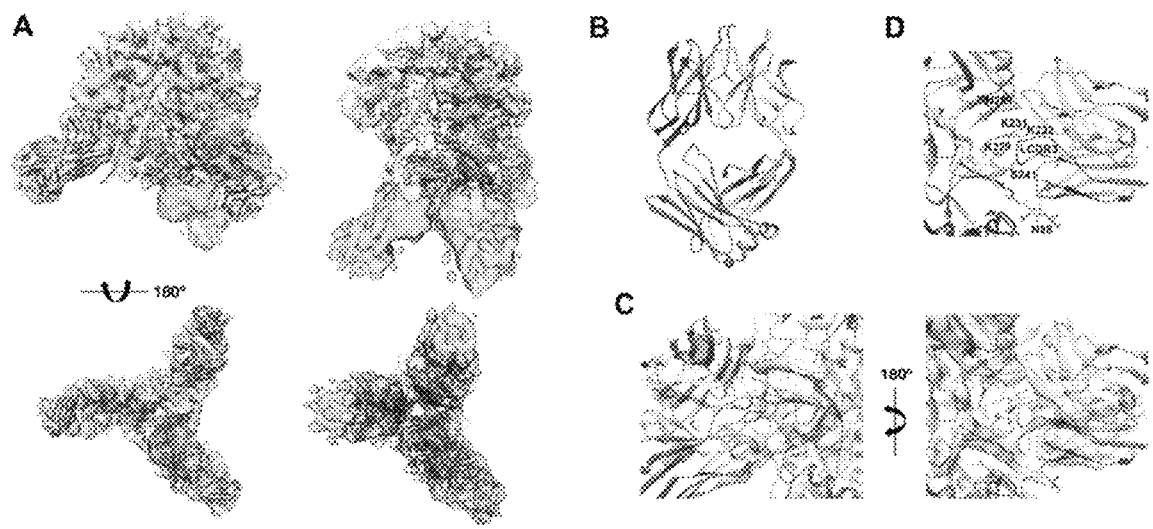
FIG. 7 depicts, in accordance with embodiments herein, structural analysis of GH epitope by cryoEM. (A) Top and side view of two representative 3D reconstructions for immune complexes with Fabs originating from PB1 of rabbit 3417. EM densities for Env are depicted in beige, for GH binding Fabs in blue, and for BOT binding Fabs in red. The crystal structure coordinates of BG505 SOSIP (PDB 518H) have been fitted into the EM densities, and are depicted as backbone in beige for gp120 and in gray for gp41. 10A light chains are colored cyan and the heavy chains in green (c.f. panel B-D). (B) Crystal structure of rabbit mAb 10A. The long LCDR3 extends away from the surface of the paratope. (C) Close-up views of a high-resolution cryoEM map of BG505 SOSIP.664 in complex with polyclonal Fabs using the cryoEM BG505 SOSIP.664 structure (PDB 5ACO) and the crystal structure of 10A fitted in. The heavy and particularly the light chain fit remarkably well into the cryoEM density, despite the polyclonal nature of the immune response and 10A having been isolated from a different rabbit. This suggests that there is a relatively consistent, molecularly similar, immunodominant rabbit response to the glycan hole of BG505. (D) Close-up view of the epitope-paratope. The long LCDR3 makes the majority of contacts with Env in a lysine-rich loop directly above the S241 glycan hole residue. The glycosylation sequon in BG505 is missing at N289, but if present would clash with the heavy chain. However, the glycan at N88 does appear to interact with the light chain.

While nsEM and 2D classification was sufficient to identify the predominant epitope specificities elicited by BG505 SOSIP.664 immunization, the inventors also performed cryoEM and 3D reconstruction of complexes from one of the serum samples (rabbit 3417, PB1) for a more detailed analysis. A dataset of ~161,000 complexes was collected and analyzed by 2D classification. The results were consistent with the nsEM data, although as expected, the cryoEM data had a much great diversity of views of the complexes due to free tumbling of the particles in solution prior to rapid-freezing, as well as a higher number of particles imaged. This relatively isotropic distribution of complexes is essential for robust 3D classification and reconstruction. A single 3D reconstruction of the entire dataset was calculated, which included a heterogeneous mixture of Env-Fab complexes, resulting in a ~4.7 Å resolution density map. The BG505 SOSIP.664 portion of this "global average" map was very well resolved and previously solved atomic structures of the trimer fit well into the map (FIG. 7A). The densities corresponding to Fabs varied between epitopes and provided a rough approximation of stoichiometry; densities that comprise the intact molecular envelope of Fabs are consistent with high stoichiometry, while incomplete molecular envelopes are consistent with lower stoichiometry but might also reflect to some degree a higher flexibility/diversity of the bound Fabs (c.f. BOT densities in FIG. 7A).

Figure 8:
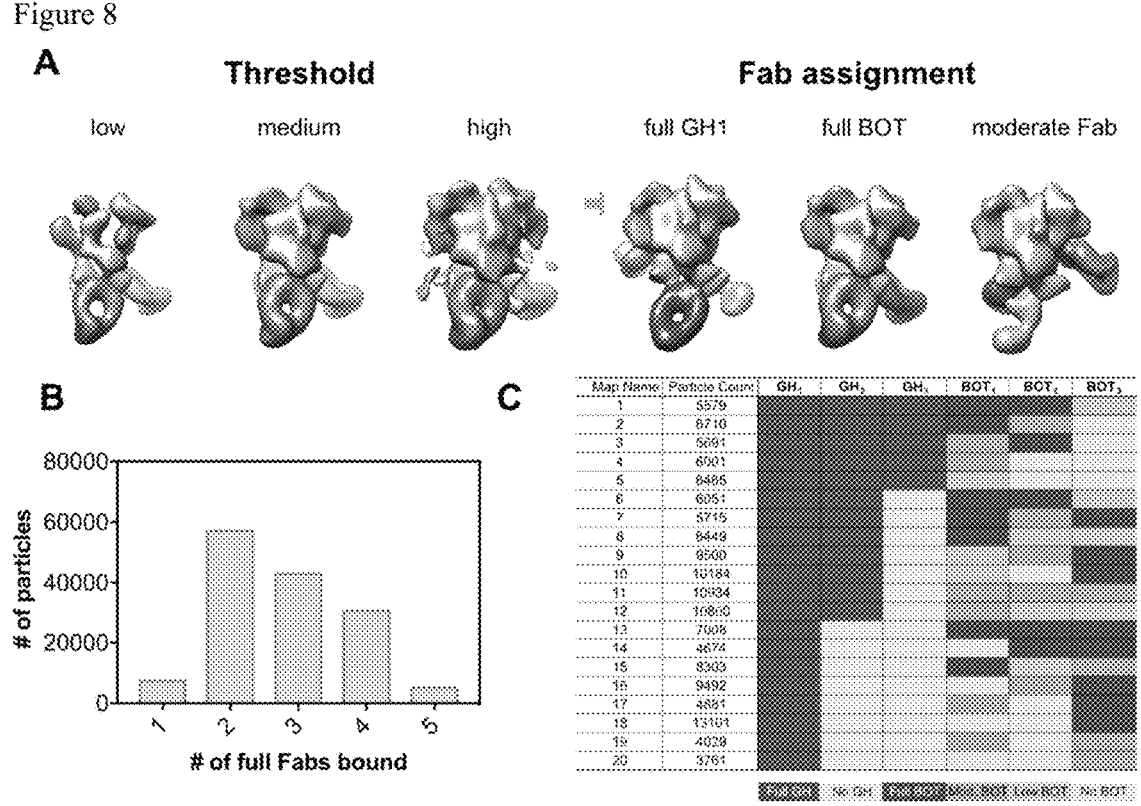
FIG. 8 depicts, in accordance with embodiments herein, semiquantitative analysis of epitope occupancy in cryoEM 3D reconstructions of immune complexes between BG505 SOSIP.664 and Fabs originating from rabbit 3417 PB1. (A) Examples of different occupancies for the indicated GH epitope. To normalize thresholds of the individual 3D reconstructions, all density maps were overlaid with a reference structure for BG505 SOSIP.664 (EMDB 8312) and adjusted in volume threshold until the Env-volumes were identical to the reference structure. Occupancy was then estimated, starting from the GH1 antibody present in all structures (referred to as $GH_1$) in a clockwise direction. (B) Number of particles displaying the indicated full occupancy. (C) Number of particles containing full (dark colors), medium, and partial occupancies (lighter colors) for each of the indicated antibody binding sites.

In one embodiment, the inventors undertook an exhaustive 3D classification approach to determine as many 3D reconstructions as possible given the size of the dataset (FIG. 11) using RELION. Based on this approach, 20 complexes were computationally isolated at moderate resolution (FIG. 11) that enabled us to observe the diversity of epitopes targeted and quantify the response to each epitope. 3D classification and refinement of the same dataset was done in CryoSparc, which resulted in 4 reconstructions that were resolved to sub-nanometer resolution. In the CryoSparc refinement, the complexes were not completely classified and, in most reconstructions, there was evidence for partial occupancy of one or more Fabs. The inventors, therefore, devised a strategy to estimate the occupancy based on the Fab density apparent at different map thresholds. Based on these analyses, the inventors semi-quantitatively report the total occupancy of the two primary antibody responses, BOT and GH (FIG. 8). It was found that, at the Fab concentration used, all immune complexes contain at least one GH1 Fab. The majority of 3D models displayed partial occupancy at one or two of the each of the potential three GH and BOT binding sites with no other pattern being discernable.

The most striking conclusion from the high-resolution analyses in CryoSparc is the high-quality density in the maps that corresponded to the GH1 antibodies, suggesting a structurally homogeneous mAb population. Further, when the high-resolution structure of 10A, which was solved by X-ray crystallography, was fit into the density map it was remarkably similar, particularly in regard to the main point of contact, the long LCDR3 loop (FIG. 7C). Notably, in HCDR1, 2, and 3, the loop lengths of the polyclonal average appeared to differ from 10A, consistent with some variation in loop length and heavy chain usage compared to 10A. These data suggest that in rabbits there may be a biased light chain usage that preferentially targets the glycan hole epitope. While the epitope-paratope regions are well resolved, for the C-terminal end of constant region 1, the 10A fit becomes poorer and densities become more diffuse, probably due to slight difference in the positions of their C-termini. Whether these differences reflect actual differences in the angle of approach of individual antibody species present in the polyclonal sera, or whether this is due to the inherent flexibility of the hinge region of the Fabs, cannot be determined from the available data. In one embodiment, at low resolution, nAbs isolated from different rabbit targeted the glycan hole in a very similar manner. As disclosed herein, in high resolution cryoEM analysis, the close resemblance of the averaged polyclonal densities with the structure of monoclonal antibody 10A, isolated from a different rabbit, is quite remarkable, suggesting highly convergent responses, even at the molecular level. This example demonstrates the power of the approach as the laborious process of isolating monoclonal antibodies for structural analysis has been circumvented.

Example 6

Analysis and Results

The rapid polyclonal imaging approach by nsEM provides a snapshot of the antibody response at any given time post vaccination and enables us to extensively and semi-quantitatively map the polyclonal immune response to a protein or glycoprotein immunogen and thereby shed new light on the epitopic diversity and maturation of antibody responses in vaccinated animals. In one embodiment, the instant approach could equally be applied to follow the course of a response during natural infection. Using this novel approach, GH1 class antibodies were confirmed as major source of neutralization in BG505 SOSIP.664-immunized rabbits. In addition, the inventors discerned differences in the kinetics by which the neutralizing antibody responses are mounted and could demonstrate that lack of neutralization in this particular case was due to a failure to mount GH-specific antibodies. Moreover, two additional classes of antibodies were identified, namely GH2 and COT1 that have not been previously described. As both new classes can be found in samples with no neutralizing activity, it suggests that these new classes of antibodies are non-neutralizing. Additional experiments with monoclonal antibodies from these classes will however be required to obtain a definitive answer about their biological activity. Besides identification of the predominantly elicited antibody classes, and the most likely source for autologous neutralization, the rapid nsEM approach as disclosed herein also provided approximate information about the avidity of the antibody classes detected. For example, this approach showed that early BOT class antibodies were inferior to GH-binding antibodies in that they disappear from immune complexes at higher Fab concentrations compared to GH class antibodies, and this property did not change throughout the course of the immunization (FIG. 10B). Moreover, the nsEM data was corroborated with occupancy data determined using a different, biochemical method. Successful epitope mapping experiments using sera from influenza A virus hemagglutinin-immunized mice, and ongoing studies investigating the humoral response to BG505 SOSIP in NHP (will both be published elsewhere), further indicate that this method is not restricted to rabbit immunoglobulin but can be applied to others species and antigens as well.

The addition of cryoEM to the instantly disclosed methodology enabled 3D reconstructions of sub-nanometer resolution that provided additional insights into the molecular recognition of the GH1-epitope on the immunogen. A high degree of structural conservation was detected in these antibodies, in particular for LCDR3. However, it remains unclear whether this is due to dominance of a single antibody clonotype, or whether different antibody clones converged to structurally similar paratopes.

While the images may not recapitulate the full diversity of antigen-specific antibodies in the serum, they likely represent a snapshot of the predominantly recognized epitopes. Thus, using the newly described work flow and a small set of SOSIP trimer constructs, it is possible to rapidly derive information to assess ongoing immunization experiments and provide data for immunogen redesign. For example, the early dominant response to the trimer base neo-epitope is concerning as activation and proliferation of BOT-specific B cells might restrict resources for B cells recognizing more productive and neutralizing epitopes. Furthermore, nearly all of the antibodies bind at an upward angle relative to the trimer. This contrasts with all known bnAbs that bind at a downward or parallel angle of approach, which reflects the fact that the soluble BG505 SOSIP.664 can be presented to rabbit B cells in an "upside-down fashion" relative to virion presentation. Therefore, particulate display of BG505 SOSIP.664 trimers may prevent presentation of the base and lower epitopes in Env and improve immune responses such that they more closely resemble neutralizing and, perhaps even to some extent, broadly neutralizing Ab responses. Overall, the rabbit responses to BG505 SOSIP.664 trimers appear quite narrow and are limited to a few epitopes. Notably, antibodies to the V3 loop were not observed, although they have been reported in ELISA binding assays. Because the complexes were formed in solution using fully native envelope trimers proteins that do not expose the V3 loop, or other epitopes that can become exposed following immobilization, this is not surprising. The instant approach therefore preferentially detects the most relevant responses to the surface of pre-fusion Env. Although there is some indication from the COT class of antibodies that less frequent antibody classes may be more challenging to detect by the instant method, they still did not go undetected (c.f. FIG. 3B, PB3 box). Additional complexes formed with epitope knock-out variants of the immunogen (FIGS. 10A and 10C), or the use of pre-adsorbed Fab preparations could also aid in the detection of rarer specificities.

In one embodiment, the instant study also showed that the kinetics of an immune response can vary. The imaging provides predictive models that accurately predict neutralization based on the epitopes targeted, at least in rabbits. Preliminary analysis of NHPs immunized with BG505 SOSIP.664 using conventional epitope mapping suggest a more diverse response than in rabbits. The presently disclosed methods can be used to interrogate NHP samples, and eventually human responses to vaccines, and inform prime-boosting strategies. For example, direct visualization may be used to rapidly decide whether a single prime is sufficient or a second "prime" should be given before introducing a heterologous boost. Further, one can determine if the elicited polyclonal antibodies directly, via epitope overlap, or indirectly, through steric blockade, may interfere with an intended epitope-focused response. Finally, comparison of imaging from human and animal model studies will reveal the similarities and differences in responses between humans and animal models and help determine the relative value of different model studies and the most appropriate animal model for iterative vaccine design including different immunization regimens and adjuvants.

Example 7

Experimental Model and Subject Details

Rabbits:

The samples used in this study derived from the previously described immunization of animals 3417 and 3420 (See McCoy et al, Holes in the native shield in the native HIV envelope are a target of trimer elicited neutralizing antibodies, Cell Rep. 2016 Aug. 30; 16(9): 2327-2338.). Briefly, New Zealand white rabbits were immunized twice with liposomes embedded with BG505 SOSIP.664 v3.2, and then received three soluble BG505 SOSIP.664 v3.2 protein boosts. The Scripps Research Institute (TSRI) Institutional Animal Care and Use Office and the Committee (IACUC) approved all experimental procedures involving rabbits 3409-3420.

Cell Lines:

TZM-bl cells were maintained at 37° C. and 5% $CO_2$ in high glucose Dulbecco's Modified Eagle Medium (DMEM, Corning) containing 1× Penicillin-Streptomycin (Corning), 2 mM L-Glutamine (Corning), and 10% heat inactivated fetal bovine serum (FBS, Omega Scientific).

Example 8

Method Details

Anti-HIV-1 Env Monoclonal Antibodies:

Monoclonal antibodies (mAbs) were expressed by co-transfection of HEK293F cells (Thermo Fisher). Briefly, 156 µg heavy chain and 156 µg light chain-expressing plasmids were mixed in 25 ml Opti-Minimum Essential Media (MEM), and then added to 25 ml Opti-MEM containing 937.5 µg Polyethylenimine (PEI) MAX 40,000 (Polysciences). After 30 min at room temperature (RT) the DNA/PEI mix was added to $10^9$ HEK293F cells in 1 L FreeStyle 293 Expression Medium (Thermo Scientific), and further incubated for 6-7 days at 37° C., 8% $CO_2$, 80% humidity, 135 rpm. Cells were then pelleted by centrifugation and filtered through 0.22 Lm Rapid-Flow filter units (Nalgene). Filtered supernatant was applied to a column containing a 1 ml packed Protein G Sepharose Fast Flow (GE Healthcare) equilibrated with phosphate-buffered saline (PBS). The column was washed with 20 column-volumes of PBS, and mAb eluted with 0.1 M glycine pH 2.5 in a 1:10 volume of 1 M Tris-HCL pH 8 solution. Antibodies were concentrated and buffer-exchanged into PBS using 10,000 MWCO Amicon Ultra-15 centrifugal filter units (EMD Millipore) over three rounds of spinning.

His-tagged Fab 10A was expressed and secreted as a soluble protein in HEK293F cells. The supernatant was concentrated and loaded onto a Ni-NTA affinity column, and the Fabs were eluted using an imidazole gradient. Next, Fabs were loaded onto a cation exchange column (monoS) and eluted using a salt gradient. Fractions containing pure Fab were pooled, concentrated and buffer exchanged into tris-buffered saline (TBS) buffer (50 mM Tris, 150 mM NaCl, pH 7.5).

Soluble Env Protein Production:

BG505 SOSIP.664 v3.2, BG505 SOSIP.664 v4.1, BG505 SOSIP.664 v5.2, BG505 SOSIP.664 v5.2 with glycans at positions N241 and N289, or BG505 MD39 CPG9 (with or without C-terminal Avi or Strep tag to enable biotinylation and purification) were used in this study. Compared to BG505 SOSIP.664 v3.2, BG505 SOSIP.664 v4.1 contains a A316W mutation, which improves hydrophobic packing and stability of the V3-loop, and a E64K mutation, which reduces spontaneous sampling of the CD4-bound "open" trimer conformation. The BG505 SOSIP.664 v5.2 is similar to the v4.1 design, with the addition of a second disulfide bond between gp120 and gp41 to further increase trimer stability. BG505 MD39 CPG9 contains the MD39 stabilizing mutations, glycans at positions N80, N241, N289, N630, and a glycosylated loop connecting gp120 and gp41 that block binding to the bottom of the trimer. BG505 trimers were expressed in HEK293F cells by transient co-transfection with furin (except for BG505 MD39 CPG9, which is cleavage independent), and then purified using methods described elsewhere, with either 2G12 or PGT145-affinity columns followed by size exclusion chromatography (SEC). Fractions corresponding to trimer were pooled and concentrated down to 1-2 mg/ml. Avi-tagged proteins were biotinylated after 2G12 or PGT145-affinity columns using the BirA biotin-protein ligase standard reaction kit (Avidity) under the following conditions and reagents from the kit: 100 µL of Avi-tagged protein, 15 µL of 10× Biomix B, 15 µl of BIO0200, 15 µl of 1 M Tris-HCL pH 8, 5 µl of BirA enzyme, incubated for 1 h at 37° C. Excess biotin and BirA enzyme was finally removed by SEC. All samples were sterile filtered prior to aliquoting and flash freezing. Structural validation of trimers was performed by analysis of negative-stain electron microscopy (EM) 2D class averages. The proteins used for immunizations had no His-tag.

Plasma or Serum IgG Purification:

IgGs were purified from plasma or serum of immunized animals using protein A and/or G sepharose resin (GE Healthcare), at a ratio of 1 ml packed resin for each ml of undiluted plasma or serum. Samples were diluted at least 4-fold in PBS, then incubated with protein A/G resin for 5 h at RT or overnight at 4° C. The resin was washed 3 times with 10 volumes PBS, and the IgGs eluted with 5-10 volumes of 0.1 M glycine pH 2.5 immediately neutralized with 1 M Tris-HCL pH 8. Buffer was exchanged to PBS or TBS either by dialysis or by centrifugation using 10 kDa cutoff membranes (Thermo Scientific) or tubes (EMD Millipore), respectively.

Fab Preparation:

Fab were prepared for EM imaging. To make Fab, IgG were digested with papain-agarose resin (Thermo Scientific) for 5 h at 37° C. using 50 µl settled resin/mg IgG in 20 mM sodium phosphate, 10 mM EDTA, 20 mM cysteine, pH 7.4. Fc and non-digested IgG were removed by 1 h incubation at RT with protein A sepharose resin (GE Healthcare), using 0.2 ml packed resin/mg of initial IgG. After protein A incubation, cysteine was removed from the flow-through containing the digested Fab by dialysis or by ultracentrifugation using 10 kDa cutoff (Thermo Scientific) or tubes (EMD Millipore), respectively.

Fab Quality Control by SDS-PAGE and SEC:

Fab size and homogeneity were assessed by Sodium Dodecyl Sulphate-PolyAcrylamide Gel Electrophoresis (SDS-PAGE) and SEC. For SDS-PAGE, 5 µg protein/lane was loaded on a 4-12% Bolt Bis-Tris Plus gel (Thermo Scientific) in reducing VS non-reducing conditions, and ran at 200 V in 3-Morpholinopropane-1-sulfonic acid (MOPS) buffer. Bands were visualized with Coomassie staining (Expedeon), and the size of the fragments evaluated by running a protein standard ladder (Thermo Scientific). For SEC, 50 µg protein was loaded on a Superdex 200 10/300 increase column using a 100 µl loop, and ran at 0.5 ml/min using an Äkta Pure system (GE Healthcare). Fab peaks were analyzed with the provided Unicorn 7.0.2 software. The size of the fragments was estimated with the help of a linear regression calculated by running a mix of proteins with known molecular weight (BioRad) on the same column.

BG505 ELISA:

High-binding enzyme-linked immunosorbent assay (ELISA) plates (Thermo Scientific) were coated with neutravidin (Thermo Scientific) or a BG505-binding antibody (mostly human PG9, PGT145, or PGT121, or rabbit 10A or 12N) overnight at 4° C., then blocked with 3% BSA for 2 h at RT. Biotinylated or untagged BG505 SOSIP.664 was captured on the neutravidin/antibody plate for 2 h at RT, before adding serial dilutions of Fab or F(ab)$_2$ for additional 2 h at RT. Binding of BG505-specific antibodies was assessed by Fab-specific secondary-horseradish peroxidase (HRP) antibodies (Jackson ImmunoResearch) after 1 h incubation at RT. HRP activity was measured by adding 3,3',5,5'-Tetramethylbenzidine (TMB)-substrate (Thermo Scientific), and blocking the reaction with 2 N sulfuric acid after 3 min incubation. OD450 was finally measured using a BioTek Synergy 2 plate reader (Perkin Elmer), and the effective concentration (EC)50 and EC90 calculated using Prism 7 software (GraphPad). Relative abundance of BG505-specific antibodies was estimated by comparing the EC50s with the ones obtained from a total IgG ELISA.

Neutralization Assays:

Replication incompetent HIV pseudovirus was produced by co-transfecting env plasmids with an env-deficient backbone plasmid (pSG3Δenv) in HEK293T cells in a 1:2 ratio, using the X-tremeGENE 9 transfection reagent (Roche). Pseudovirus was harvested after 48-72 h by sterile-filtration (0.22 µm) of cell culture supernatants, and titrated on TZM-bl cells. Neutralization was then assessed by TZM-bl assay: previously titrated pseudovirus were incubated with Fab for 1 h at 37° C., and then transferred in a white 384-well plate (Greiner Bio-One) together with an equal volume of TZM-bl cells (4,000/well) resuspended in complete DMEM+20 µg/ml Diethylaminoethyl (DEAE)-dextran. After 48 h at 37° C. and 5% $CO_2$, the supernatant was removed and the cells lysed with Glo lysis buffer (Promega) for 5 min at RT. Luciferase activity was measured by the addition of Bright-Glo luciferase-substrate (Promega), and the luminescence signal read using a BioTek Synergy 2 plate reader. Full IgG and F(ab)$_2$ were used as control, and uninfected cells to correct for background.

Occupancy Standard Curve:

Twelve molar excess (for each mAb) of a single or combination of mAbs known to bind with different stoichiometries were incubated with 10 µg BG505 trimers overnight at RT in 100 µl total volume. Complexes were then ran on a Superose 6 10/300 increase column and Äkta Pure system (GE Healthcare) and the different elution peaks used to calculate a stoichiometry standard curve using the Prism 7 software (GraphPad).

Complexes for EM:

10 µg BG505 trimers were incubated overnight at RT with 2000-fold $EC_{50}$ excess of Fab in 100 µl total volume, and then the complexes purified on a Superose 6 10/300 increase column and Äkta Pure system (GE Healthcare) in TBS buffer. The fractions containing the complexes were pooled in 10 kDa cutoff tubes (EMD Millipore) and concentrated down to 50 µl final volume.

X-Ray Crystallography:

Fab 10A was crystallized from solutions containing 10 mg/ml Fab in TBS buffer. Crystals were grown using sitting drop vapor diffusion with a well solution containing 0.1 M sodium citrate pH 5.26, 0.17 M ammonium acetate, 15% glycerol and 19% PEG4000. Crystals were grown at 298 K and appeared within 3 days. Fab 10A crystals were cryoprotected by soaking in a well solution supplemented with 30% glycerol. Diffraction data were collected at the Advanced Photon Source (APS) beamline 23ID-D. Data collection and processing statistics are detailed in Table 2. Data sets were indexed, integrated, and scaled using the HKL-2000 package. The structures were solved by molecular replacement using PHASER with homology models for Fab 10A (SWISS-MODEL) as search models and further refined using phenix.refine combined with manual building cycles in Coot.

TABLE 2

X-ray data collection and refinement statistics for Fab 10A.

| Data collection | Fab10A |
|---|---|
| Beamline | APS 23ID-D |
| Wavelength (Å) | 1.03315 |
| Space group | P1 |
| Unit cell parameters(Å, °) | a = 51.17, b = 63.56, c = 72.65, α = 67.99, β = 87.87, γ = 76.74 |
| Resolution (Å) | 40.7-1.80 (1.83-1.80)$^a$ |
| Unique reflections | 73,928 (3,385)$^a$ |
| Redundancy | 3.2 (2.6)$^a$ |
| Completeness (%) | 96.3 (87.8)$^a$ |
| $<I/\sigma_I>$ | 16.5 (1.0)$^a$ |
| $R_{sym}^b$ (%) | 7.4 (93.8)$^a$ |
| $R_{pim}^b$ (%) | 4.8 (66.1)$^a$ |
| $CC_{1/2}^c$ (%) | 85.6 (32.9)$^a$ |

TABLE 2-continued

X-ray data collection and refinement statistics for Fab 10A.

| Data collection | Fab10A |
|---|---|
| Refinement statistics | |
| Reflections (work) | 70,071 |
| Reflections (test) | 3,841 |
| $R_{cryst}{}^d/R_{free}{}^e$ (%) | 16.0/21.0 |
| No. of atoms | |
| Protein | 6,415 |
| Water | 547 |
| Ligands | 18 |
| Average B-value (Å²) | |
| Protein | 36 |
| Water | 41 |
| Ligands | 48 |
| Wilson B-value (Å²) | 27 |
| RMSD from ideal geometry | |
| Bond length (Å) | 0.010 |
| Bond angle (°) | 1.04 |
| Ramachandran statistics (%) | |
| Favored | 96.68 |
| Outliers | 0.12 |

[a] Numbers in parentheses refer to the highest resolution shell.
[b] $R_{sym} = \Sigma_{hkl} \Sigma_i | I_{hkl, i} - <I_{hkl}> | / \Sigma_{hkl} \Sigma_i I_{hkl, i}$ and $R_{pim} = \Sigma_{hkl} (1/(n-1))^{1/2} \Sigma_i | I_{hkl, i} - <I_{hkl}> | / \Sigma_{hkl} \Sigma_i I_{hkl, i}$, where $I_{hkl, i}$ is the scaled intensity of the $i^{th}$ measurement of reflection h, k, l, $<I_{hkl}>$ is the average intensity for that reflection, and n is the redundancy.
[c] $CC_{1/2}$ = Pearson correlation coefficient between two random half datasets.
[d] $R_{cryst} = \Sigma_{hkl} | F_o - F_c | / \Sigma_{hkl} | F_o | \times 100$, where $F_o$ and $F_c$ are the observed and calculated structure factors, respectively.
[e] $R_{free}$ was calculated as for $R_{cryst}$, but on a test set comprising 5% of the data excluded from refinement.
[f] Calculated from MolProbity {Chen: 2010cha}

Negative Stain EM:

SEC purified complexes were deposited at roughly 0.04 mg/mL onto carbon coated copper grids and stained with 2% (w/v) uranyl formate for 30 sec as previously described. Grids were imaged at 120 KeV using a Tecnai Spirit using Leginon. Images were collected on a 4k×4k TemCam F416 detector and transferred into the Appion database for initial image processing. Particles were picked using DoG Picker and 2D classes were generated using MSA/MRA. Particles corresponding to Env-Fab complexes were selected and further processed via 3D classification in Relion to separate out the unique complexes within the heterogeneous dataset before final refinement of each map. Figures were prepared using UCSF Chimera.

Figure 11:
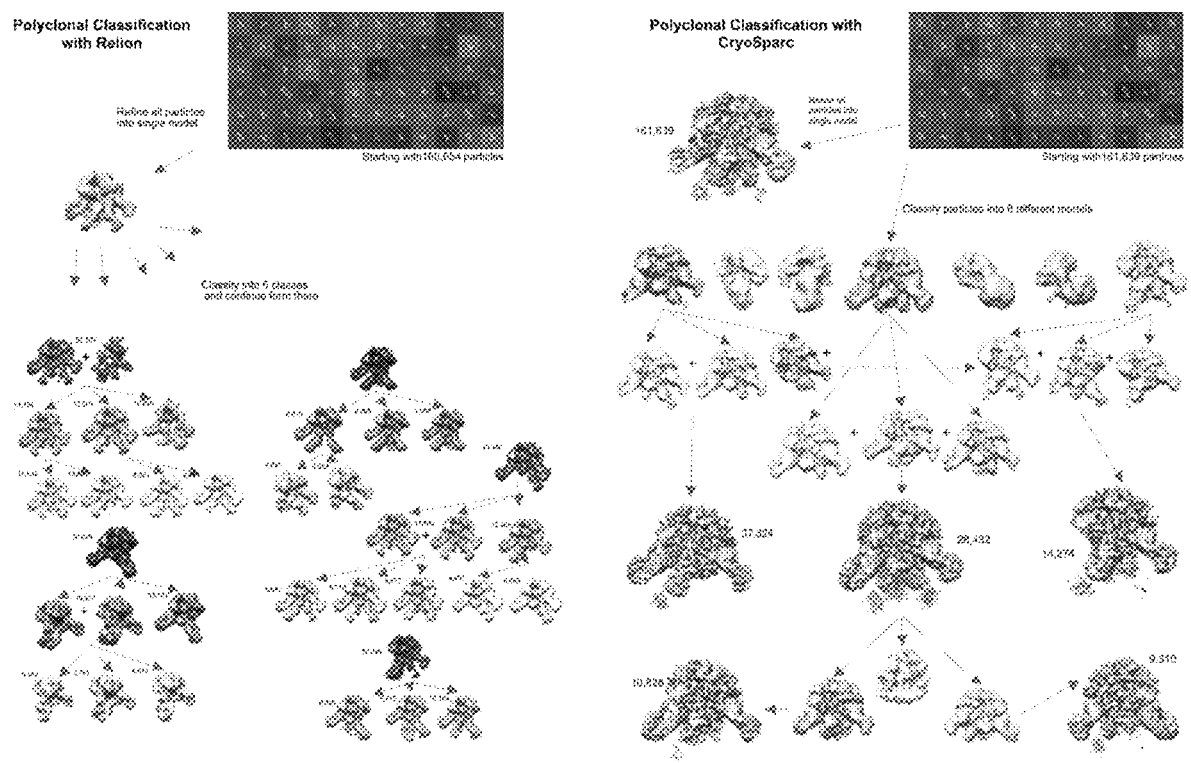
FIG. 11 depicts, in accordance with embodiments herein, generation and refinement of 3D models from cryoEM using Relion (left) and CryoSparc (right) software. Relion is a software developed by MRC Laboratory of Molecular Biology; CryoSparc is a software by Structura Biotechnology Inc.

Cryo EM:

The 3417 PB1 sample was concentrated to 5.6 mg/ml. Immediately before deposition onto a 1.2/1.3 200 Quantifoil grid (EMS) that were glow discharged for 10 sec, 3 L of the concentrated complex was mixed with 1 μL of 0.42 mM Dodecyl Maltoside (DDM, Anatrace). Addition of DDM promoted appearance of complexes into holes and improved angular sampling of individual complexes. Grids were then blotted and plunged into liquid ethane using a Vitrobot (FEI) to capture complexes in vitreous ice. Cryo girds were transferred into a 200 KeV Talos Artica and images recorded on a 3710×3838 pixel Gatan K2 Summit detector using Leginon at a defocus range of −1.5 μm to −2.5 μm. Images were transferred to the Appion database and particles were picked using DoG Picker and placed into a stack. Initial 2D classification was conducted in Relion and non-Env particles were removed, creating a clean stack of 170,078 particles that was then subjected to 3D classification. The first round of 3D classification resulted in six reconstructions. Subsequent rounds of sequential 3D classification were conducted as illustrated in FIG. 11. 3D reconstructions with similar occupancy of bound Fabs were combined before final refinement. This approach resulted in 20 unique 3D reconstructions that were then used to quantify the Fabs at each epitope.

The same cryo particle stack was also subjected to image processing in CryoSparc that resulted in 4 subnanometer resolution reconstructions (FIG. 11). In one embodiment, the inventors calculated a global average of all particles that was resolved to 4.71 Å resolution.

Fab Occupancy Analysis:

Within the 20 Relion cryoEM maps there was still obvious sub-stoichiometric occupancy of Fabs in different epitopes. A method was derived to approximate the occupancy of the Fabs at each site to get a better estimate of the total response per epitope. In the end each epitope was characterized as having full, moderate, low, or no occupancy using the following approach. Each reconstruction was normalized to best match the trimer density of a 20 Å resolution low pass filtered map of BG505 SOSIP.664. In every map, at these normalized thresholds, the inventors saw at least one nicely resolved GH Fab. At this contour level there were Fabs present at other epitopes that only had partial density. Once the density threshold (higher sigma density) was increased, the inventors saw that the GH Fab density persisted, thus they consider this fully occupied. Conversely, the partial density Fabs would disappear at this higher threshold, and it was therefore considered this partial occupancy. To detect even less occupancy the threshold was decreased (lower sigma signal) relative to the normalized map and if density appeared at an epitope that began to resemble a Fab the inventors considered this low occupancy. If no density appeared, then it was characterized as no occupancy. These results are summarized in FIG. 8.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of mapping antibody binding to an immunogen, the method comprising:
   immunizing a subject with an immunogen;
   obtaining sera from the immunized subject at multiple time intervals following immunization, wherein the sera comprises antibodies that bind to the immunogen;
   isolating one or more antibodies from the sera;
   contacting the one or more antibodies with the immunogen to form one or more immune complexes;
   imaging, by electron microscopy, the one or more immune complexes from each of the multiple time intervals to obtain structural images;
   determining, from a plurality of structural images, immunogen-antibody binding sites for each of the immune complexes obtained at the multiple time intervals;
   mapping immunogen-antibody binding by comparing structural images obtained at the multiple time intervals to determine changes in immunogen-antibody binding over the multiple time intervals.

2. The method of claim 1, wherein the serum antibodies comprise IgA (immunoglobin A), IgD (immunoglobin D), IgE (immunoglobin E), IgG (immunoglobin G), IgM (immunoglobin M), or combinations thereof.

3. The method of claim 1, wherein the immune complex is purified by a chromatographic method prior to imaging.

4. The method of claim 3, wherein the chromatographic method comprises size exclusion chromatography (SEC).

5. The method of claim 1, wherein the electron microscopy comprises cyro electron microscopy or negative stain electron microscopy.

6. The method of claim 1, wherein the immune complex is further analyzed by Mass Spectrometry, next generation sequencing (NGS), MS/MS and/or NGS-assisted MS/MS.

7. The method of claim 1, wherein the subject is a human, mouse, humanized mouse, rat, or humanized rat.

8. The method of claim 1, further comprising characterizing the antibody type and quantifying the antibody response to the immunogen.

9. The method of claim 1, wherein the subject is a mammal.

10. The method of claim 1, wherein the immunogen is a recombinant immunogen.

11. The method of claim 1, wherein the immunogen is an epitope and/or an antigen.

12. The method of claim 1, wherein the method maps the epitope binding sites on the antibody.

* * * * *